US010736844B2

(12) United States Patent
Anderson et al.

(10) Patent No.: US 10,736,844 B2
(45) Date of Patent: Aug. 11, 2020

(54) COMPOSITIONS AND METHODS FOR TREATING VIRAL INFECTIONS

(75) Inventors: David E. Anderson, Boston, MA (US); Tanvir Ahmed, Nepean (CA); Jasminka Bozic, Ottawa (CA); Marc Kirchmeier, Harleysville, PA (US)

(73) Assignee: VARIATION BIOTECHNOLOGIES INC., Ottawa (CA)

( * ) Notice: Subject to any disclaimer, the term of this patent is extended or adjusted under 35 U.S.C. 154(b) by 169 days.

(21) Appl. No.: 13/979,322

(22) PCT Filed: Jan. 13, 2012

(86) PCT No.: PCT/US2012/021388
§ 371 (c)(1),
(2), (4) Date: Jul. 11, 2013

(87) PCT Pub. No.: WO2012/097346
PCT Pub. Date: Jul. 19, 2012

(65) Prior Publication Data
US 2013/0295165 A1 Nov. 7, 2013

Related U.S. Application Data

(60) Provisional application No. 61/432,567, filed on Jan. 13, 2011.

(51) Int. Cl.
*A61K 45/00* (2006.01)
*A61K 9/127* (2006.01)
(Continued)

(52) U.S. Cl.
CPC .......... *A61K 9/127* (2013.01); *A61K 39/0015* (2013.01); *A61K 39/12* (2013.01);
(Continued)

(58) Field of Classification Search
None
See application file for complete search history.

(56) References Cited

U.S. PATENT DOCUMENTS 3,952,097 A 4/1976 Levy
4,024,241 A 5/1977 Levy
(Continued)

FOREIGN PATENT DOCUMENTS

CA 2258907 A1 12/1997
CN 101574394 A 11/2009
(Continued)

OTHER PUBLICATIONS

Hofland et al., "Nonionic Surfactant Vesicles: A Study of Vesicle Formation, Characterization, and Stability," Journal of Colloid and Interface Science, vol. 161, Issue 2: 366-376 (1993)(abstract only).*
(Continued)

*Primary Examiner* — M Franco G Salvoza
(74) *Attorney, Agent, or Firm* — Choate, Hall & Stewart LLP; Charles E. Lyon; Rolando Medina

(57) ABSTRACT

The present disclosure provides compositions and methods useful for treating viral infections. As described herein, the compositions and methods are based on the development of immunogenic compositions that include an attenuated or inactivated virus in combination with a non-ionic surfactant vesicle (NISV).

8 Claims, 5 Drawing Sheets

| STORAGE TEMPERATURE (° C) | 4 | 25 | 40 | 4 | 25 | 40 | 4 | 25 | 40 |
|---|---|---|---|---|---|---|---|---|---|
| FORMULATION | REFERENCE VACCINE (UNFORMULATED CONTROL) | | | NO NISVs FORMULATION CONTROL | | | NISVs FORMULATION | | |
| TOTAL LIPID CONTENT | NONE | | | NONE | | | 12.5 mg | | |

(51) Int. Cl.
*A61K 39/00* (2006.01)
*A61K 39/12* (2006.01)
*A61K 47/14* (2017.01)

(52) U.S. Cl.
CPC ...... *A61K 47/14* (2013.01); *A61K 2039/5254* (2013.01); *A61K 2039/545* (2013.01); *A61K 2039/55555* (2013.01); *Y02A 50/388* (2018.01)

(56) References Cited

U.S. PATENT DOCUMENTS

| | | | |
|---|---|---|---|
| 4,349,538 A | 9/1982 | Levy | |
| 4,352,884 A | 10/1982 | Nakashima et al. | |
| 4,436,727 A | 3/1984 | Ribi | |
| 4,537,769 A | 8/1985 | Cerini | |
| 4,866,034 A | 9/1989 | Ribi | |
| 4,877,611 A | 10/1989 | Cantrell | |
| 4,894,228 A | 1/1990 | Purcell et al. | |
| 4,912,094 A | 3/1990 | Myers et al. | |
| 4,983,387 A | 1/1991 | Goldstein et al. | |
| 5,057,540 A | 10/1991 | Kensil et al. | |
| 5,160,669 A | 11/1992 | Wallach et al. | |
| 5,250,236 A | 10/1993 | Gasco | |
| 5,340,588 A | 8/1994 | Domb | |
| 5,393,527 A | 2/1995 | Malick et al. | |
| 5,393,530 A | 2/1995 | Schneider et al. | |
| 5,549,910 A | 8/1996 | Szoka, Jr. | |
| 5,567,434 A | 10/1996 | Szoka, Jr. | |
| 5,653,996 A | 8/1997 | Hsu | |
| 5,679,355 A | 10/1997 | Alexander et al. | |
| 5,817,318 A | 10/1998 | Sia et al. | |
| 5,853,753 A | 12/1998 | Maierhofer et al. | |
| 5,858,368 A | 1/1999 | Smith et al. | |
| 5,861,243 A | 1/1999 | Dietrich et al. | |
| 5,876,721 A | 3/1999 | Alexander et al. | |
| 5,879,703 A | 3/1999 | Fountain | |
| 5,910,306 A | 6/1999 | Alving et al. | |
| 5,919,480 A | 7/1999 | Kedar et al. | |
| 5,948,410 A | 9/1999 | Van Scharrenburg et al. | |
| 5,962,298 A | 10/1999 | Fiers et al. | |
| 5,977,081 A | 11/1999 | Marciani | |
| 6,005,099 A | 12/1999 | Davies et al. | |
| 6,080,725 A | 6/2000 | Marciani | |
| 6,090,392 A | 7/2000 | Berman | |
| 6,136,606 A | 10/2000 | Chatfield | |
| 6,180,110 B1 | 1/2001 | Funkhouser et al. | |
| 6,207,178 B1 | 3/2001 | Westesen et al. | |
| 6,235,888 B1 | 5/2001 | Pachuk et al. | |
| 6,248,363 B1 | 6/2001 | Patel et al. | |
| 6,287,570 B1 | 9/2001 | Foley | |
| 6,290,967 B1 | 9/2001 | Volkin et al. | |
| 6,303,347 B1 | 10/2001 | Johnson et al. | |
| 6,344,354 B1 | 2/2002 | Webster et al. | |
| 6,372,223 B1 | 4/2002 | Kistner et al. | |
| 6,383,806 B1 | 5/2002 | Rios | |
| 6,500,623 B1 | 12/2002 | Tung | |
| 6,503,753 B1 | 1/2003 | Rios | |
| 6,534,065 B1 | 3/2003 | Makin et al. | |
| 6,538,123 B2 | 3/2003 | Barban | |
| 6,541,003 B1 | 4/2003 | Smith | |
| 6,605,457 B1 | 8/2003 | Fiers et al. | |
| 6,635,246 B1 | 10/2003 | Barrett et al. | |
| 6,649,410 B2 | 11/2003 | Rios | |
| 6,653,130 B2 | 11/2003 | Rios | |
| 6,692,955 B1 | 2/2004 | Meredith et al. | |
| 6,706,859 B1 | 3/2004 | Sorensen | |
| 6,740,325 B1 | 5/2004 | Arnon et al. | |
| 6,743,900 B2 | 6/2004 | Burt et al. | |
| 6,764,840 B2 | 7/2004 | Johnson et al. | |
| 6,787,351 B2 | 9/2004 | Chen et al. | |
| 6,831,169 B2 | 12/2004 | Pachuk et al. | |
| 6,861,244 B2 | 3/2005 | Barrett et al. | |
| 6,991,929 B1 | 1/2006 | D'Hondt | |
| 7,052,701 B2 | 5/2006 | Barrett et al. | |
| 7,063,849 B1 | 6/2006 | Thibodeau et al. | |
| 7,067,134 B1 | 6/2006 | Kang et al. | |
| 7,192,595 B2 | 3/2007 | Arnon et al. | |
| 7,244,435 B2 | 7/2007 | Lai | |
| 7,262,045 B2 | 8/2007 | Schwartz et al. | |
| 7,316,813 B2 | 1/2008 | Eichhorn | |
| 7,348,011 B2 | 3/2008 | Guntaka et al. | |
| 7,361,352 B2 | 4/2008 | Birkett et al. | |
| 7,399,840 B2 | 7/2008 | Burt et al. | |
| 7,468,259 B2 | 12/2008 | Fiers et al. | |
| 7,494,659 B2 | 2/2009 | Katinger et al. | |
| 7,510,719 B2 | 3/2009 | Dang et al. | |
| 7,514,086 B2 | 4/2009 | Arnon et al. | |
| 7,527,800 B2 | 5/2009 | Yang et al. | |
| 7,537,768 B2 | 5/2009 | Luke et al. | |
| 9,610,248 B2 | 4/2017 | Anderson et al. | |
| 2002/0164648 A1 | 11/2002 | Goins et al. | |
| 2003/0092145 A1 | 5/2003 | Jira et al. | |
| 2004/0011840 A1 | 1/2004 | Lovett | |
| 2004/0022840 A1 | 2/2004 | Nagy et al. | |
| 2004/0081688 A1 | 4/2004 | Del Curto et al. | |
| 2005/0042230 A1 | 2/2005 | Anderson et al. | |
| 2005/0095283 A1* | 5/2005 | Castor et al. | 424/450 |
| 2005/0169979 A1 | 8/2005 | Michaeli et al. | |
| 2005/0214331 A1 | 9/2005 | Levy | |
| 2006/0121105 A1 | 6/2006 | Barenholz et al. | |
| 2006/0257852 A1* | 11/2006 | Rappuoli et al. | 435/5 |
| 2007/0142315 A1 | 6/2007 | Forsbach et al. | |
| 2007/0224257 A1 | 9/2007 | Commander et al. | |
| 2007/0264273 A1 | 11/2007 | Barenholz et al. | |
| 2008/0057080 A1 | 3/2008 | Luke et al. | |
| 2008/0131466 A1 | 6/2008 | Reed et al. | |
| 2008/0145375 A1 | 6/2008 | Bembridge et al. | |
| 2008/0160089 A1 | 7/2008 | Vitiello et al. | |
| 2008/0181914 A1 | 7/2008 | Eichhorn | |
| 2008/0213461 A1 | 9/2008 | Gill et al. | |
| 2008/0268028 A1 | 10/2008 | Zurbriggen et al. | |
| 2008/0286353 A1 | 11/2008 | Gregoriadis | |
| 2009/0028903 A1 | 1/2009 | Hanon et al. | |
| 2009/0041809 A1 | 2/2009 | Emtage | |
| 2009/0081157 A1 | 3/2009 | Kornbluth et al. | |
| 2009/0081254 A1 | 3/2009 | Vajdy et al. | |
| 2009/0117141 A1 | 5/2009 | Torres et al. | |
| 2009/0130146 A1* | 5/2009 | Broeker | A61K 39/12 424/217.1 |
| 2009/0155309 A1 | 6/2009 | Friede et al. | |
| 2009/0181078 A1 | 7/2009 | Reed et al. | |
| 2009/0202620 A1* | 8/2009 | Turnell et al. | 424/450 |
| 2010/0062071 A1 | 3/2010 | Loxley et al. | |
| 2010/0080844 A1 | 4/2010 | Bacon et al. | |
| 2010/0129392 A1 | 5/2010 | Shi et al. | |
| 2010/0226932 A1 | 9/2010 | Smith et al. | |
| 2011/0177163 A1* | 7/2011 | Diaz-Mitoma et al. | 424/451 |
| 2012/0156240 A1 | 6/2012 | Anderson et al. | |
| 2012/0177683 A1 | 7/2012 | Anderson et al. | |
| 2012/0276125 A1 | 11/2012 | Ast et al. | |
| 2013/0108692 A1 | 5/2013 | Anderson et al. | |
| 2013/0323280 A1 | 12/2013 | Anderson et al. | |
| 2014/0356399 A1 | 12/2014 | Anderson | |
| 2015/0079077 A1 | 3/2015 | Kirchmeier et al. | |
| 2018/0256723 A1 | 9/2018 | Anderson | |

FOREIGN PATENT DOCUMENTS

| | | | | |
|---|---|---|---|---|
| EP | 0413637 A1 | 2/1991 | | |
| EP | 0 433242 A1 | 6/1991 | | |
| EP | 729473 A1 | 9/1996 | | |
| EP | 1 129 723 A1 | 9/2001 | | |
| EP | 2 014 279 A1 | 1/2009 | | |
| GB | 2122204 A | 1/1984 | | |
| WO | WO-198806882 A1 | 9/1988 | | |
| WO | WO-90/02965 A1 | 3/1990 | | |
| WO | WO-92/00081 A1 | 1/1992 | | |
| WO | WO-1993019781 A1 | 10/1993 | | |
| WO | WO-95/09651 A1 | 4/1995 | | |
| WO | WO-95/14026 A1 | 5/1995 | | |
| WO | WO-95/17210 A1 | 6/1995 | | |
| WO | WO-96/11280 A1 | 4/1996 | | |
| WO | WO 9704768 A1 * | 2/1997 | | A61K 9/1272 |
| WO | WO-98/01139 A1 | 1/1998 | | |

(56) References Cited

FOREIGN PATENT DOCUMENTS

| | | | | |
|---|---|---|---|---|
| WO | WO-98/50399 A1 | | 11/1998 | |
| WO | WO-99/62500 A1 | | 12/1999 | |
| WO | WO 0105374 A1 | * | 1/2001 | ........... A61K 9/1272 |
| WO | WO-02/051390 A2 | | 7/2002 | |
| WO | WO-03/011223 A2 | | 2/2003 | |
| WO | WO-03/099195 A2 | | 12/2003 | |
| WO | WO-2005/117958 A1 | | 12/2005 | |
| WO | WO-2007/110776 A1 | | 10/2007 | |
| WO | WO-2008/153236 A1 | | 12/2008 | |
| WO | WO-2009/029695 A1 | | 3/2009 | |
| WO | WO-2009/091531 A2 | | 7/2009 | |
| WO | WO-2009/155489 A2 | | 12/2009 | |
| WO | WO-2010/033812 A1 | | 3/2010 | |
| WO | WO-2011/005769 A1 | | 1/2011 | |
| WO | WO-2012/006367 A2 | | 1/2012 | |
| WO | WO-2012/006368 A2 | | 1/2012 | |
| WO | WO-2012/097347 A1 | | 7/2012 | |
| WO | WO-2013/104995 A2 | | 7/2013 | |
| WO | WO-2013/111012 A2 | | 8/2013 | |

OTHER PUBLICATIONS

International Preliminary Report on Patentability for PCT/US2012/21388, dated Jul. 16, 2013 (7 pages).
Collins et al., Non-Ionic Surfactant Vesicle Formulation of Stibogluconate for Canine Leishmaniases, J. Pharm. Pharmacol., 42 (Supplement):53P (1990).
International Search Report for PCT/US2012/21388, dated May 8, 2012 (4 pages).
Kirby et al., Dehydration-Rehydration Vesicles: A Simple Method for High Yield Drug Entrapment in Liposomes, Biotechnology, 2:979-984 (1984).
Pick, Liposomes with a Large Trapping Capacity Prepared by Freezing and Thawing of Sonicated Phospholipid Mixtures, Arch. Biochem. Biophys., 212(1):186-194 (1981).
Russell et al., Effective Immunization Against Cutaneous Leishmaniases with Defined Membrane Antigens Reconstituted into Liposomes, J. Immunol., 140:1274-1279 (1988).
Schalk et al., Estimation of the Number of Infectious Measles Viruses in Live Virus Vaccines Using Quantitative Real-Time PCR, Journal of Virological Methods, 117:179-187 (2004).
World Health Organization, The Immunological Basis for Immunization Series, Model 7: Measles (2009).
International Search Report for PCT/US09/57492, 2 pages (dated Nov. 20, 2009).
Mann et al., Optimisation of a Lipid Based Oral Delivery System Containing A/Panama Influenza Haemagglutinin, Vaccine, 22: 2425-2429 (2004).
Tarekegn, A. et al., Niosomes in Targeted Drug Delivery: Some Recent Advances, International Journal of Pharmaceutical Sciences and Research, 1(9): 1-8 (2010).
Written Opinion for PCT/US09/57492, 5 pages (dated Nov. 20, 2009).
Alexopoulou et al., Preparation and characterization of lyophilized liposomes with incorporated quercetin, J Liposome Res. 16(1): 17-25 (2006).
Alpan et al., The role of dentritic cells, B cells, and M cells in gut-oriented immune responses, J. Immunol., 166(8): 4843-4852 (2001).
Andre et al., Inactivated candidate vaccines for hepatitis A, Prog. Med. Virol., 37: 72-95 (1990).
Bangham et al., Diffusion of univalent ions across the lamellae of swollen phospholipids, J. Mol. Biol. 13(1): 238-252 (1965).
Chen et al., An overview of liposome lyophilization and its future potential, Journal of Controlled Release, 142: 299-311 (2010).
Chen et al., Research advances on Solid lipid nanoparticles as new drug carrier, Chinese Journal of Ethnomedicine and Ethnopharmacy, 2: 7-10 (2009).
Cregg et al., High-Level Expression and Efficient Assembly of Hepatitis B Surface Antigen in the Methylotrophic Yeast, Pichia Pastoris, Biotechnology, 5: 479-485 (1987).
Fattovich, G., Natural history of hepatitis B, J. Hepatol., 39 Suppl 1: S50-S58 (2003).
Field, et al., Inducers of interferon and host resistance. II. Multistranded synthetic polynucleotide complexes, Proc. Natl. Acad. Sci. USA, 58(3): 1004-1010 (1967).
Harford et al., Expression of hepatitis B surface antigen in yeast, Dev. Biol. Stand., 54: 125-130 (1983).
Hassan, Y. et al., Immune responses in mice induced by HSV-1 glycoproteins presented with ISCOMs or NISV delivery systems, Vaccine, 14(17-18): 1581-1589 (1996).
Hilleman MR., Critical overview and outlook: pathogenesis, prevention, and treatment of hepatitis and hepatocarcinoma caused by hepatitis B virus, Vaccine, 21(32): 4626-4649 (2003).
Huckriede, A. et al., The virosome concept for influenza vaccines, Vaccine, 23 Suppl 1:S26-38 (2005).
Jurk, et al., Modulating Responsiveness of Human TLR7 and 8 to Small Molecule Ligands With T-rich Phosphorothiate Oligodeoxynucleotides, Eur. J. Immunol., 36(7): 1815-26 (2006).
Kasrian and Deluca, The Effect of Tertiary Butyl Alcohol on the Resistance of the Dry Product Layer During Primary Drying, Pharm. Res., 12(4): 491-495 (1995).
Kasrian and Deluca, Thermal Analysis of the Tertiary Butyl Alcohol-Water System and Its Implications on Freeze-Drying, Pharm. Res., 12(4): 484-490 (1995).
Khmelnitsky et al., Denaturation capacity: a new quantitative criterion for selection of organic solvents as reaction media in biocatalysis, European Journal of Biochem., 198: 31-41 (1991).
Lasic, D.D., Novel Applications of Lipsomes, TIBTECH, 16:307-321 (1998).
Lavanchy, The Importance of Global Surveillance of Influenza, Vaccine, 17: S24-S25 (1999).
Levy et al., Inhibition of Tumor Growth by Polyinosinic-Polycytidylic Acid, Proc. Natl. Acad. Sci. USA, 62:357-361 (1969).
Li and Deng, A novel method for the preparation of liposomes: freeze drying of monophase solutions, J. Pharm. Sci., 93(6): 1403-1414 (2004).
Mao et al., Further evaluation of the safety and protective efficacy of live attenuated hepatitis A vaccine (H2-strain) in humans, Vaccine, 15(9): 944-947 (1997).
McAleer et al., Human hepatitis B vaccine from recombinant yeast, Nature, 307(5947): 178-180 (1984).
Miller et al., Hepatitis C virus shares amino acid sequence similarity with pestiviruses and flaviviruses as well as members of two plant virus supergroups, Proc. Natl. Acad. Sci., 87: 2057-2061 (1990).
Mowat, A.M., Dendritic cells and immune responses to orally administered antigens, Vaccine, 23(15): 1797-1799 (2005).
Oku, et al., Effect of serum protein binding on real-time trafficking of liposomes with different charges analyzed by positron emission tomography, Biochimica et Biophysica Acta, 1280:149-154 (1996).
Provost et al., New findings in live, attenuated hepatitis A vaccine development, J. Med. Virol., 20(2): 165-175 (1986).
Salager, J-L., Surfactants—Types and Uses, FIRP Booklet #E300-A, Teaching Aid in Surfactant Science & Engineering, in English, Laboratory of Formulation, Interfaces, Rheology and Processes, Universidad de Los Andes, 2: 1-50 (2002).
Schubert et al., Solvent Injection as a New Approach for Manufacturing Lipid Nanoparticles—Evaluation of the Method and Process Parameters, European Journal of Pharmaceuticals and Biopharmaceutics, 55:125-131 (2003).
Szoka, Jr., F. and Papahadjopoulos, D., Comparative Properties and Methods of Preparaton of Lipid Vesicles (Liposomes)1, Ann. Rev. Viophys. Bioeng., 9:467-508 (1980).
Uchegbu, I.F. and Vyas, S.P., Non-ionic surfactant based vesicles (niosomes) in drug delivery, in International Journal of Pharmaceuticals, 172:33-70 (1998).
Valenzuela et al., Chemical synthesis of a gene for human epidermal growth factor urogastrone and its expression in yeast, Proc. Natl. Acad. Sci. USA, 80(24): 7461-7465 (1983).
Vangala et al., A comparative study of cationic liposome and niosome-based adjuvant systems for protein subunit vaccines: char-

(56) References Cited

OTHER PUBLICATIONS acterisation, environmental scanning electron microscopy and immunisation studies in mice, Journal of Pharmacy and Pharmacology, 58:787-799, (2006).
Varun et al., Niosomes and Liposomes—Vesicular Approach Towards Transdermal Drug Delivery, International Journal of Pharmaceutical and Chemical Sciences, 1(3): 632-644 (2012).
Verma, S. et al., Nanoparticle vesicular systems: A versatile tool for drug delivery, Journal of Chemical and Pharmaceutical Research, 2(2):496-509 (2010).
Wagner et al., Liposome Technology for Industrial Purposes, J. Drug Delivery, vol. 2011, Article ID 591325 (9 pages) (2010).
Walde et al., Enzymes Inside Lipid Vesicles: Preparation, Reactivity and Applications, Biomol. Eng., 18:143-177 (2001).
Wang et al., Solvent Injection-Lyophilization of Tert-Butyl Alcohol/ Water Cosolvent Systems for the Preparation of Drug-Loaded Solid Lipid Nanoparticles, Colloids and Surfaces B: Biointerfaces, 79:254-261 (2010).
Weiner et al., Variable and hypervariable domains are found in the regions of HCV corresponding to the flavivirus envelope and NS1 proteins and the pestivirus envelope glycoproteins, Virology 180(2): 842-848 (1991).
Yan et al., Recent Advances in Liposome-Based Nanoparticles for Antigen Delivery, Polymer Reviews, 47(3): 329-344 (2007).
Kumar, G.P. et al., Nonionic surfactant vesicular systems for effective drug delivery—an overview, Acta Pharmaceutica Sinica B, 1(4): 208-219 (2011).
Mozafari, M.R., Nanomaterials and Nanosystems for Biomedical Applications, Springer, 1-159 (2007).
Anderson, R.J., Properties of Cholesterol Obtained from Different Sources, J. Biol. Chem., 71: 4007-418 (1927).
Bennett, E. et al., Translational modifications to improve vaccine efficacy in an oral influenza vaccine, methods, 49: 322-327 (2009).
Bramwell, V. et al., Particulate delivery systems for vaccines: what can we expect?, The Journal of Pharmacy and Pharmacology, 58(6): 717-728 (2006).
CAS Registry 18656-38-7, Record for Dimyristoyl phosphatidylcholine, 2 pages (Nov. 16, 1984).
Conacher, M. et al., Oral immunisation with peptide and protein antigens by formulation in lipid vesicles incorporating bile salts (bilosomes), Vaccine, 19(20-22): 2965-2974 (2001).
Gnjatic, S. et al., TLR Agonists, the Cancer Journal, 16(4): 382-391 (2010).
Israelachvili, J.N. et al., Physical Principles of Membrane Organization, Quarterly Reviews of Biophysics, 13(2): 121-200 (1980).
Jiang et al., Advances in non-ionic surfactant based vesicles, Chinese Journal of Modern Drug Application, 1:(11): 98-101 (2007). English Translation, pp. 1-8.
Manosroi, A. et al., Characterization of vesicles prepared with various non-ionic surfactants mixed with cholesterol, Colloids and Surfaces B: Biointerfaces, 30(1-2): 129-138 (2003).
Senior, J. and Radomsky, M., Liposomes for Local Sustained Drug Release, Sustained-Release Injectable Products, Chapter 7: 137-180 (Published Sep. 30, 2005).
Van Hal, D. A. et al., Preparation and Characterization of Nonionic Surfactant Vesicles, Journal of Colloid and Interface Science, 178(1): 263-273 (1996).
Martin, F. J. and MacDonald, R. C., Lipid vesicle-cell interactions. III. Introduction of a new antigenic determinant into erythrocyte membranes, the Journal of cell biology, 70: 515-526 (1976).
Yingzheng, Z. Biopharmaceutical Preparation, Zhejiang University Press, 1st edition, p. 73 (Jun. 2011). [No known English translation].

* cited by examiner

COMPOSITIONS AND METHODS FOR TREATING VIRAL INFECTIONS

CROSS REFERENCE TO RELATED APPLICATIONS

This application is the National Stage of International Application No. PCT/US2012/021388, filed Jan. 13, 2012, which claims priority under 35 U.S.C. § 119(e) to U.S. provisional application Ser. No. 61/432,567, filed Jan. 13, 2011, the entire contents of each of which are hereby incorporated by reference.

BACKGROUND

Measles, mumps and rubella are three common childhood diseases that are caused by viral infection (by measles virus (a paramyxovirus), mumps virus (a paramyxovirus), and rubella virus (a togavirus), respectively). Measles, mumps and rubella infections may cause serious medical complications which may lead to death. Measles is an infection of the respiratory system and causes symptoms including fever, cough, runny nose, and general rash, and commonly leads to complications such as pneumonia and encephalitis. Mumps is an infection that causes symptoms including inflammation, fever, headache and orchitis, and can lead to complications such as aseptic meningitis and deafness. Rubella, commonly known as German measles, generally causes mild symptoms, although infection of a mother during pregnancy can be quite serious.

Vaccines against measles, mumps and rubella are produced from live attenuated viruses which have been propagated in cell substrates. Each component of MMR vaccine is initially prepared in the monovalent form, each of which is then mixed together to produce a trivalent form in which the component virus population is present in a well defined quantity sufficient to induce an effective immune response in a vaccine recipient. The marketed MMR vaccines are presented as a lyophilized vial, which has to be kept at 2-8° C. for no more than 3 years as per the licensure indications. However several factors including stabilizer composition, storage conditions and residual moisture can affect the thermal stability of the lyophilized vaccine. The World Health Organization (WHO) recommends tissue culture infective doses ($TCID_{50}$) assay using Vero cells for evaluating potency of live measles virus in the vaccine. However, the potency measurements may vary depending on the method of determination, the laboratory, and the conditions at the time of the test.

WHO has set up minimum requirements for vaccine stability in freeze dried form as well as when reconstituted as a liquid solution prior to administration. In the freeze dried state, current measles vaccines must retain a minimum potency of at least 3.0 $log_{10}$ virus particles per human dose after exposure to a temperature of 37° C. for at least one week and the virus titre dose not decrease by more than 1.0 $log_{10}$ during incubation. However, reconstituted measles vaccines quickly lose potency at exposure to room temperatures. At 22° C. to 25° C. the vaccine loses approximately 50% of potency in one hour. At temperatures over 37° C. the vaccine is inactivated within one hour (The Immunological Basis for Immunization Series, Module 7: Measles (WHO/EPI/GEN/93.17).

Several attenuated measles, mumps and rubella (MMR) vaccines are currently licensed and have been successful in reducing the incidence of viral infection. However, all vaccines, including attenuated virus vaccines, lose potency over time and the rate of potency loss is temperature-dependent. Therefore, cold-chain systems have been established to ensure that the potency of vaccines is maintained by storing them under refrigerated conditions (in most cases between 2 and 8° C.) until the point of use. Establishing a cold chain for vaccine storage and distribution is a major undertaking and maintenance is difficult. It is also apparent that, despite best efforts, cold chains do not always function as intended for many reasons, such as improperly maintained or outdated refrigeration equipment, power outages resulting in equipment failure, poor compliance with cold-chain procedures and inadequate monitoring. The result is that vaccines in the cold chain are often subjected to temperature excursions (i.e., temperatures outside of the target range).

While attenuated measles, mumps and rubella (MMR) vaccines have been successful in reducing the incidence of disease worldwide, there remains a need in the art for improved vaccines that are stable and retain potency when exposed to high temperatures.

SUMMARY

The present disclosure provides compositions and methods useful for treating viral infections (e.g., those caused by measles, mumps, or rubella viruses). As described herein, the compositions and methods are based on the development of immunogenic compositions that include an attenuated or inactivated virus in combination with a non-ionic surfactant vesicle (NISV). In certain embodiments at least a portion of the viral antigen present in the composition is physically associated with the NISV. In certain embodiments the compositions are lyophilized and subsequently rehydrated after a period of storage. In certain embodiments the rehydrated compositions exhibit greater potency as compared to otherwise equivalent compositions that lack the NISV. In certain embodiments the lyophilized compositions are stored at temperatures in excess of 8° C. prior to rehydration. In certain embodiments the rehydrated compositions exhibit greater potency as compared to otherwise equivalent compositions that lack the NISV and that were also stored at temperatures in excess of 8° C. prior to rehydration. In certain embodiments the viral antigen is taken from a licensed vaccine and the administered dose of viral antigen is less than the standard human dose for the licensed vaccine.

DEFINITIONS

Figure 1:
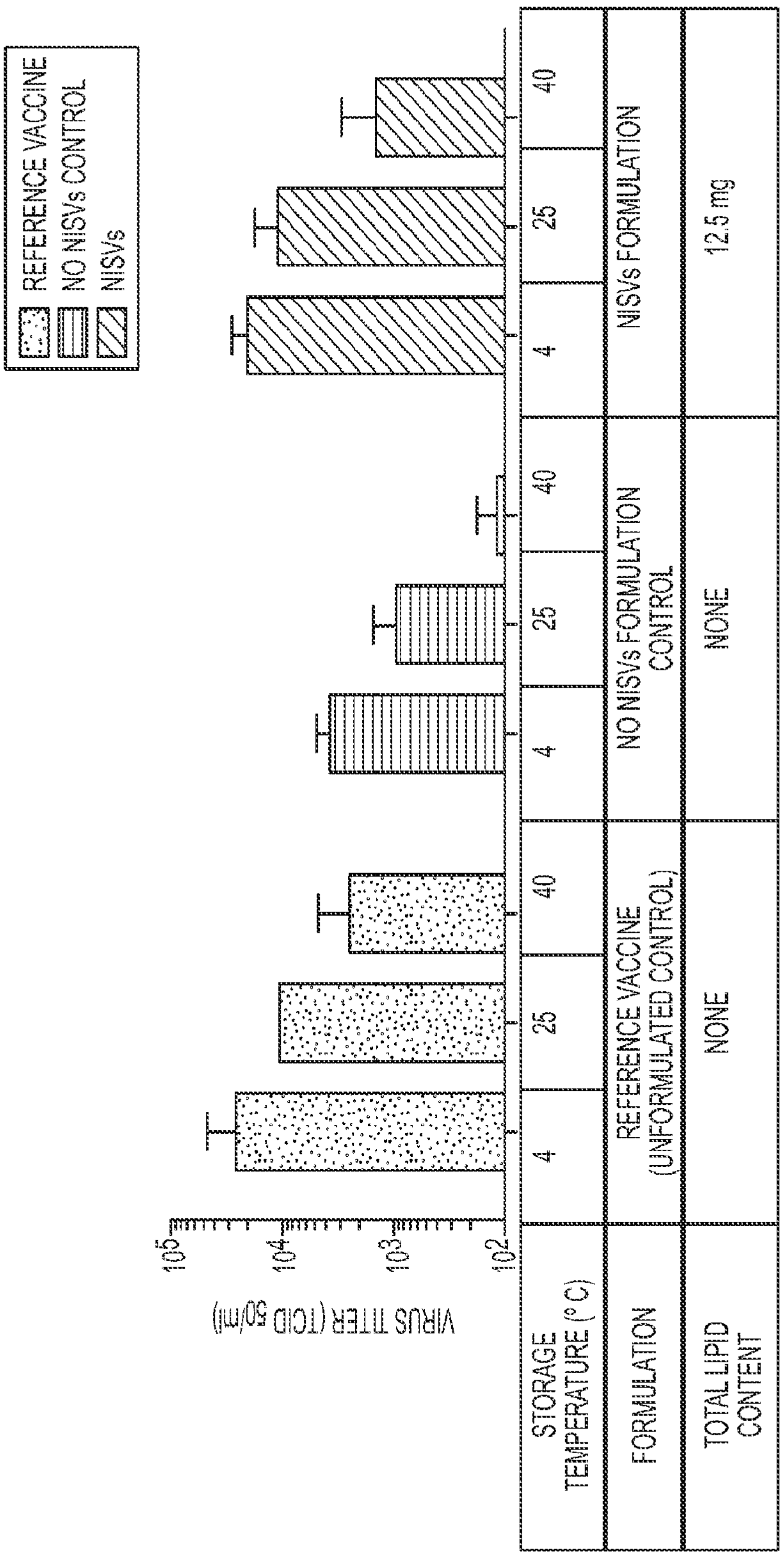
FIG. 1 shows the results from a measles potency assay ($TCID_{50}$) that was performed using different reformulated M-M-R-II® vaccines that had been stored at about 4° C., about 25° C. and about 40° C. for 2 weeks.

Throughout the present disclosure, several terms are employed that are defined in the following paragraphs.

As used herein, the term "antigen" or "viral antigen" refers to a substance containing one or more epitopes that can be recognized by an antibody. In certain embodiments, an antigen can be a virus. The term "antigen" encompasses inter alia attenuated and inactivated viruses. In certain embodiments, an antigen may be an "immunogen."

As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum).

As used herein, the term "immunogenic" means capable of producing an immune response in a host animal against a non-host entity (e.g., a viral antigen). In certain embodiments, this immune response forms the basis of the protective immunity elicited by a vaccine against a specific infectious organism (e.g., a virus).

As used herein, the terms "therapeutically effective amount" refer to the amount sufficient to show a meaningful benefit in a subject being treated. The therapeutically effective amount of an immunogenic composition may vary depending on such factors as the desired biological endpoint, the nature of the composition, the route of administration, the health, size and/or age of the subject being treated, etc.

As used herein, the term "treat" (or "treating", "treated", "treatment", etc.) refers to the administration of a composition to a subject who has a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to the vaccination of a subject.

DETAILED DESCRIPTION OF CERTAIN EMBODIMENTS

The present disclosure provides compositions and methods useful for treating viral infections (e.g., infections by measles, mumps, and/or rubella viruses). As described herein, the compositions and methods are based on the development of immunogenic compositions that include an attenuated or inactivated virus in combination with a non-ionic surfactant vesicle (NISV). In certain embodiments at least a portion of the antigen present in the composition is physically associated with the NISV. In certain embodiments the compositions are lyophilized and subsequently rehydrated after a period of storage. In certain embodiments the rehydrated compositions exhibit greater potency as compared to otherwise equivalent compositions that lack the NISV. In certain embodiments the lyophilized compositions are stored at temperatures in excess of 8° C. prior to rehydration. In certain embodiments the rehydrated compositions exhibit greater potency as compared to otherwise equivalent compositions that lack the NISV and that were also stored at temperatures in excess of 8° C. prior to rehydration. In certain embodiments the viral antigen is taken from a licensed vaccine and the administered dose of viral antigen is less than the standard human dose for the licensed vaccine.

I. Viral Antigens

Measles, Mumps, Rubella and Varicella Viral Antigens

In some embodiments, the compositions and methods of the present disclosure may be used with one or more antigens included in a vaccine that is licensed or under development. Table 1 is a non-limiting list of vaccines that are licensed or under development for measles, mumps, rubella and varicella infections.

TABLE 1

| Vaccine | Disease |
|---|---|
| Attenuvax ® | Measles |
| Diplovax HDC 4.0 ® | Measles |
| Morbilvax ® | Measles |
| Rimevax ® | Measles |
| M-R-Vax, M-R-VaxII ® | Measles and Rubella |
| Moru-Viraten ® | Measles and Rubella |
| M-M-R Vax ® | Measles, Mumps and Rubella |
| M-M-R-II ® | Measles, Mumps and Rubella |
| M-M-RvaxPRO ® | Measles, Mumps and Rubella |
| Priorix ® | Measles, Mumps and Rubella |
| Trimovax ® | Measles, Mumps and Rubella |
| Triviraten Berna ® | Measles, Mumps and Rubella |
| ProQuad ® | Measles, Mumps, Rubella and Varicella |
| Mumpsvax ® | Mumps |
| Rubilin ® | Mumps and Rubella |
| Meruvax II ® | Rubella |
| Ervevax ® | Rubella |
| R-Vac ® | Rubella |
| Varivax ® | Varicella |

In the following sections we discuss these and other exemplary viral antigens that could be used in compositions or methods of the present disclosure.

In the United States, a measles, mumps and rubella (MMR) vaccine was first licensed in 1971, with a second dose of the vaccine introduced in 1989. In general, in countries where childhood MMR vaccination is routine, the incidence of measles, mumps and rubella has dramatically decreased (e.g., by more than 99% in 1995 as compared to the number of cases in 1941).

Several attenuated measles, mumps and rubella (MMR) vaccines are currently licensed. For example, M-M-R-II® is developed and manufactured by Merck & Co., Inc. M-M-R-II® contains a sterile lyophilized preparation of (1) Attenuvax® (Measles Virus Vaccine Live) an attenuated line of measles virus, (2) Mumpsvax® (Mumps Virus Vaccine Live) a strain of mumps virus propagated in chick embryo cell culture, and (3) Meruvax II® (Rubella Virus Vaccine Live) an attenuated strain of rubella virus. Each 0.5 mL dose contains not less than 1,000 $TCID_{50}$ (50% tissue culture infectious dose) of measles virus, not less than 5,000 $TCID_{50}$ of mumps virus, and not less than 1,000 $TCID_{50}$ of rubella virus. Upon reconstitution, M-M-R-II® (as with other licensed MMR vaccines) is typically administered subcutaneously. Although one dose of M-M-R-II® in children over 12 months of age generally induces the production of neutralizing antibodies, some patients fail to seroconvert after the first dose. Accordingly, a second booster is recommended, especially prior to elementary school entry, in order to seroconvert those who did not respond to the first dose. In order to ensure that there is no loss of potency of the M-M-R-II® vaccine, it must be maintained at a temperature of 10° C. or colder during shipment, maintained at a temperature of 2° C. to 8° C. during storage in a lyophilized state, and used within 8 hours after reconstitution.

Another example of an MMR vaccine, PROQUAD® which also contains a Varicella component has been licensed and sold in the Unites States by Merck, although production is currently suspended. PROQUAD® is administered once in children over 12 months of age, with an optional booster administered at least three months later.

In one aspect, the present application provides immunogenic compositions that include an attenuated or inactivated virus. It is to be understood that immunogenic compositions provided by the present disclosure may include one or more components of an MMR vaccine (e.g., measles, mumps, or rubella virus, or a combination thereof). In some embodiments, immunogenic compositions include a varicella virus component (e.g., alone, such as with VARIVAX®, or in combination with other virus components, such as with PROQUAD®).

As mentioned above, all known licensed MMR vaccines include attenuated viruses. It is to be understood that any one of these licensed vaccines may be combined with a vesicle as described herein to produce an immunogenic composition. For example, commercial M-M-R-II® may be combined in this manner to produce an immunogenic composition. In some embodiments, licensed vaccines are first purified (e.g., to remove alum adjuvant or other reagents in the vaccine). In some embodiments, licensed vaccines are not purified prior to formulation with a vesicle as described herein.

As is well known in the art, the advantage of an attenuated virus lies in the potential for higher immunogenicity which results from its ability to replicate in vivo without causing a full infection. One method which has been used in the art to prepare attenuated viruses is viral adaptation which involves serially passing a viral strain through multiple cell cultures. Over time the strain mutates and attenuated strains can then be identified. For example, in preparing M-M-R-II®, an attenuated strain of measles virus is propagated in chick embryo cell culture, a B level strain of mumps is propagated in chick embryo cell culture, and an attenuated strain of rubella is propagated in human diploid lung fibroblasts. In certain embodiments the virus may be passed through different cell cultures.

It will be appreciated that any measles, mumps, and/or rubella virus strain may be used, e.g., without limitation any of the following strains which have been described in the art:

Measles virus Enders' attenuated Edmonston strain (AttA)
Measles virus attenuated AIK-C strain
Mumps virus Jeryl Lynn (B-level) strain
Mumps virus Leningrad Zagreb strain
Mumps virus Urabe Am 9 strain
Rubella virus Wistar RA 27/3 strain
Rubella virus Giguere; 1964 United States
Rubella virus HPV-77; 1961 United States
Rubella virus Judith; 1963 Liverpool U.K.
Rubella virus KO-1; 1967 Kochi, Japan While all currently licensed MMR vaccines include attenuated viruses, alternative vaccines which include inactivated viruses may be used in accordance with the present disclosure. In certain embodiments, an immunogenic composition may comprise such an inactivated virus. It will be appreciated that any method may be used to prepare an inactivated virus. In general, these methods will involve propagating a virus in a host cell, lysing the host cell to release the virus, isolating and then inactivating the virus. The virus is typically harvested from cell cultures and screened for infectious dosage as well as for the absence of adventitious agents. Chemical treatment of the virus (e.g., formalin, formaldehyde, among others) is commonly used to inactivate the virus. However, it is to be understood that other techniques could be used, e.g., treatment with chlorine, exposure to high temperatures, etc.

Other Viral Antigens

Table 2 is a non-limiting list of other live attenuated vaccines that are licensed or under development. It is to be understood that immunogenic compositions provided by the present disclosure may include one or more components of these vaccines.

TABLE 2

| Vaccine | Disease |
|---|---|
| DA2PPC | Canine Distemper, Adenovirus type 2, Parainfluenza, Canine Parvovirus, and Canine Coronavirus |
| RotaTeq ® | Rotavirus |
| Rotarix ® | Rotavirus |
| Zostavax ® | Shingles |
| Dryvax ® | Smallpox and Monkeypox |
| YF-Vax ® | Yellow Fever |
| PRRS Virus Vaccine | Porcine Reproductive and Respiratory Syndrome Virus |
| PR Virus Vaccine | PseudoRabies Virus |

Canine distemper is a disease caused by viral infection by canine distemper virus, which is a paramyxovirus that is closely related to measles virus. Canine distemper virus may cause serious medical conditions affecting a variety of mammalian species including dogs, weasels, skunks, hyenas, raccoons, and non-domestic felines. Canine distemper infection may causes symptoms including fever, anorexia, runny nose, and eye discharge, and commonly leads to complications such as pneumonia and encephalitis. An attenuated canine distemper vaccine has been licensed, including a multivalent DA2PPC vaccine, which protects against canine distemper (D), adenovirus type 2 (A2), parainfluenza (P), canine parvovirus (P) and canine coronavirus (C). It is to be understood that immunogenic compositions provided by the present disclosure may include one or more components of DA2PPC (e.g., a canine distemper virus antigen).

Rotavirus infection leads to rotavirus gastroenteritis, which can be especially severe in infants and young children. Licensed live attenuated vaccines for treatment of rotavirus infection include RotaTeq® and Rotarix®. RotaTeq® is indicated for the prevention of rotavirus gastroenteritis caused by the G1, G2, G3, and G4 serotypes of the virus. RotaTeq® is administered orally in a three-dose series to infants between the ages of 6 to 32 weeks. Each 2 ml dose of RotaTeq® contains a live reassortant virus, containing G1, G2, G3, G4, and HA and contains a minimum of $2.0–2.8\times10^6$ infectious units (IU). Rotarix® is indicated for the prevention of rotavirus gastroenteritis caused by G1, G3, G4, and G9 serotypes of the virus. Rotarix® is administered orally in a two-dose series to infants between the ages of 6 weeks and 24 weeks of age.

Each 1 ml dose of Rotarix® contains a minimum of $10^6$ $CCID_{50}$ of live, attenuated human G1P rotavirus.

Shingles is a viral infection of the nerve roots, which typically causes pain and rash on one side of the body. Shingles is most common in older adults and people with weak immune systems. A licensed virus for treatment of shingles caused by herpes zoster virus infection is Zostavax®, which is a lyophilized preparation of the Oka/Merck strain of live, attenuated varicella-zoster virus. Zostavax® is indicated for subcutaneous administration and is indicated for individuals 60 years of age and older. Each 0.65 ml dose of Zostavax® contains at least 19,400 pfu of live, attenuated virus.

Another example of a licensed live attenuated vaccine is DRYVAX®, which is a live-virus preparation of vaccinia virus for treatment of smallpox virus infection. DRYVAX® is prepared from calf lymph which is purified, concentrated, and dried by lyophilization. The reconstituted vaccine has been shown to contain not more than 200 viable bacterial organisms per ml. DRYVAX® is intended for multiple-puncture use, i.e., administration of the vaccine into the superficial layers of the skin using a bifurcated needle. Typically, vaccination with DRYVAX® results in viral multiplication, immunity, and cellular hypersensitivity. With the primary vaccination, a papule appears at the site of vaccination on about the 2nd to 5th day. This becomes a vesicle on the 5th or 6th day, which becomes pustular, umbilicated, and surrounded by erythema and induration. The maximal area of erythema is attained between the 8th and 12th day following vaccination (usually the 10th). The erythema and swelling then subside, and a crust forms which comes off about the 14th to 21st day. At the height of the primary reaction known as the Jennerian response, there is usually regional lymphadenopathy and there may be systemic manifestations of fever and malaise. Primary vaccination with DRYVAX® at a potency of 100 million pock-forming units (pfu)/ml has been shown to elicit a 97% response rate by both major reaction and neutralizing antibody response in children.

Yet another example of a licensed live attenuated vaccine is YF-VAX® for treatment of yellow fever virus infections. YF-YAX® is prepared by culturing the 17D strain of yellow fever virus in living avian leukosis virus-free chicken embryos. YF-VAX® is lyophilized and sealed under nitrogen for storage and is reconstituted immediately prior to use. YF-VAX® is formulated to contain not less than 5.04 $Log_{10}$ pfu per 0.5 ml dose. Typically, immunity to yellow fever develops by the tenth day after primary vaccination with YF-VAX®. Although it has been demonstrated that yellow fever vaccine immunity can persist for at least 30-35 years, and in some cases for life, booster vaccinations are required at intervals of 10 years in order to boost antibody titer.

Porcine reproductive and respiratory syndrome virus (PRRSV), also known as blue-ear pig disease is a virus that causes a disease of pigs, called porcine reproductive and respiratory syndrome (PRRS). This economically important, pandemic disease causes reproductive failure in breeding stock and respiratory tract illness in young pigs. A live attenuated vaccine has been developed to prevent PRRS.

Pseudorabies is a viral disease in swine that is endemic in most parts of the world. It is caused by Suid herpesvirus 1 (SuHV-1), which is also called Pseudorabies virus (PRV) and is also known as Aujeszky's disease, and in cattle as mad itch. Other domestic and wild mammals, such as cattle, sheep, goats, cats, dogs, and raccoons, are also susceptible where the disease is usually fatal. Research on PRV in pigs has pioneered animal disease control with live attenuated vaccines. Although the word "pseudorabies" means "false rabies," or "rabies-like," it is a misnomer. Pseudorabies is related to the herpes virus, not the rabies virus.

II. Vesicles

In general, immunogenic compositions of the present disclosure include a non-ionic surfactant vesicle (NISV). As is well known in the art, vesicles generally have an aqueous compartment enclosed by one or more bilayers which include amphipathic molecules. Any non-ionic surfactant with appropriate amphipathic properties may be used to form such a vesicle. In some embodiments, at least a portion of the viral antigen present in the composition is associated with the vesicle (i.e., encapsulated within an aqueous core of the vesicle and/or associated with a vesicle bilayer). These embodiments are encompassed by the term "antigen-containing vesicle." In certain embodiments an immunogenic composition may also include amounts or components of the viral antigen that are not associated with a vesicle.

Without limitation, examples of suitable surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary surfactant is 1-monopalmitoyl glycerol.

Ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

It is also to be understood that vesicles may also incorporate an ionic amphiphile, e.g., to cause the vesicles to take on a negative charge. For example, this may help to stabilize the vesicles and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic amphiphile, if present, will typically comprise, between 1 and 50% by weight of the non-ionic surfactant (e.g., 1-5%, 1-10%, 1-15%, 1-20, 1-25%, 1-30%, 1-35%, 1-40%, 1-45%, 5-10%, 5-15%, 5-20%, 5-25%, 5-30%, 5-35%, 5-40%, 5-45%, 5-50%, 10-15%, 10-20%, 10-25%, 10-30%, 10-35%, 10-40%, 10-45%, 10-50%, 15-20%, 15-25%, 15-30%, 15-35%, 15-40%, 15-45%, 15-50%, 20-25%, 20-30%, 20-35%, 20-40%, 20-45%, 20-50%, 25-30%, 25-35%, 25-40%, 25-45%, 25-50%, 30-35%, 30-40%, 30-45%, 30-50%, 35-40%, 35-45%, 35-50%, 40-45%, 40-50%, or 45-50%).

To form vesicles, the components may be admixed with an appropriate hydrophobic material of higher molecular mass capable of forming a bi-layer (such as a steroid, e.g., a sterol such as cholesterol). The presence of the steroid assists in forming the bi-layer on which the physical properties of the vesicle depend. The steroid, if present, will typically comprise between 20 and 120% by weight of the non-ionic surfactant (e.g., 20-30%, 20-40%, 20-50%, 20-60%, 20-70%, 20-80%, 20-90%, 20-100%, 20-110%, 30-40%, 30-50%, 30-60%, 30-70%, 30-80%, 30-90%, 30-100%, 30-110%, 30-120%, 40-50%, 40-60%, 40-70%, 40-80%, 40-90%, 40-100%, 40-110%, 40-120%, 50-60%, 50-70%, 50-80%, 50-90%, 50-100%, 50-110%, 50-120%, 60-70%, 60-80%, 60-90%, 60-100%, 60-110%, 60-120%, 70-80%, 70-90%, 70-100%, 70-110%, 70-120%, 80-90%, 80-100%, 80-110%, 80-120%, 90-100%, 90-110%, 90-120%, 100-110%, 100-120%, or 110-120%).

In certain embodiments, the vesicles comprise a non-ionic surfactant, an ionic amphiphile and a steroid. In certain embodiments, the vesicles comprise 1-monopalmitoyl glycerol, dicetylphospate and cholesterol.

In certain embodiments, the vesicles consist essentially of a non-ionic surfactant, an ionic amphiphile and a steroid. In certain embodiments, the vesicles consist essentially of 1-monopalmitoyl glycerol, dicetylphospate and cholesterol.

In certain embodiments, the vesicles do not comprise a transport enhancing molecule which facilitates the transport of lipid-like molecules across mucosal membranes. In some embodiments, the vesicles do not comprise a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles do not comprise acyloxylated amino acids, such as acylcarnitines and salts thereof, and palmitoylcarnitines.

Methods for Making Vesicles

It will be appreciated that there are known techniques for preparing vesicles comprising non-ionic surfactants, such as those referred to in PCT Publication No. WO93/019781. An exemplary technique is the rotary film evaporation method, in which a film of non-ionic surfactant is prepared by rotary evaporation from an organic solvent, e.g., a hydrocarbon or chlorinated hydrocarbon solvent such as chloroform, e.g., see Russell and Alexander, *J. Immunol.* 140:1274, 1988. The resulting thin film is then rehydrated in bicarbonate buffer optionally in the presence of viral antigen.

Another method for the production of vesicles is that disclosed by Collins et al., *J. Pharm. Pharmacol.* 42:53, 1990. This method involves melting a mixture of the non-ionic surfactant, steroid (if used) and ionic amphiphile (if used) and hydrating with vigorous mixing in the presence of aqueous buffer.

Another method involves hydration in the presence of shearing forces. An apparatus that can be used to apply such shearing forces is a well known, suitable equipment (see, e.g., PCT Publication No. WO88/06882). Sonication and ultra-sonication are also effective means to form the vesicles or to alter their particle size.

In certain embodiments, at least a portion of the viral antigen is associated with lipid vesicles (where, as used herein, the term "association" encompasses any form of physical interaction). In certain embodiments, at least a portion of the viral antigen is entrapped within lipid vesicles. Association and entrapment may be achieved in any manner. For example, in the rotary film evaporation technique, this can be achieved by hydration of the film in the presence of antigen. In other methods, the viral antigen may be associated with preformed vesicles by a dehydration-rehydration method in which viral antigen present in the aqueous phase is entrapped by flash freezing followed by lyophilization, e.g., see Kirby and Gregoriadis, *Biotechnology* 2:979, 1984. Alternatively a freeze thaw technique may be used in which vesicles are mixed with the viral antigen and repeatedly flash frozen in liquid nitrogen, and warmed to a temperature of the order of, e.g., 60° C. (i.e., above the transition temperature of the relevant surfactant), e.g., see Pick, *Arch. Biochem. Biophys.* 212:195, 1981.

In certain embodiments, vesicles for use in accordance with the present invention are prepared by a method that includes: melting the non-ionic surfactant (optionally with a steroid and/or an ionic amphiphile, collectively the "lipids") to produce a molten mixture; combining the molten mixture with an aqueous solution that includes a viral antigen; and homogenizing the resulting product. In certain embodiments, the molten mixture is are added to the aqueous solution that includes the viral antigen. In certain embodiments, aqueous solution that includes the viral antigen is added to the molten mixture.

In certain embodiments, the molten mixture and aqueous solution are combined in relative amounts and volumes that achieve a lipid concentration of at least about 5 mg/ml in the resulting product. Indeed, through experimentation and as described in the Examples, we have found that when the lipids and viral antigen are homogenized with a lipid concentration in excess of 5 mg/ml the resulting compositions tend to be more thermostable than when a lower lipid concentration is used (see Examples). In some embodiments, therefore, the present invention provides desirable compositions (specifically including thermostable compositions) comprising a viral antigen and vesicles, which compositions contain a specified lipid concentration established herein to impart particular characteristics (e.g., improved thermostability) to the compositions.

In certain embodiments, a lipid concentration of at least about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 mg/ml is achieved. In certain embodiments, the lipid concentration is in a range of about 5 mg/ml to about 10, 11, 12, 13, 14, 15, 16, 17, 18, 19, 20, or 25 mg/ml. In certain embodiments, the lipid concentration is in a range of about 5, 6, 7, 8, 9, 10, 11, 12, 13, 14, 15 mg/ml to about 30 mg/ml. In certain embodiments, the lipid concentration is in a range of about 5 mg/ml to about 50 mg/ml, about 5 mg/ml to about 25 mg/ml, about 10 mg/ml to about 50 mg/ml, about 10 mg/ml to about 30 mg/ml, or about 10 mg/ml to about 50 mg/ml.

In some embodiments, the non-ionic surfactant (optionally with other components such as a steroid and/or an ionic amphiphile) is melted at a temperature range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.). In some embodiments, the non-ionic surfactant (optionally with other components such as a steroid and/or an ionic amphiphile) is melted at about 120° C., at about 125° C., at about 130° C., at about 135° C., at about 140° C., at about 145° C. or at about 150° C.

In some embodiments, the aqueous solution comprising a viral antigen is temperature controlled. In some embodiments, the aqueous solution comprising a viral antigen is kept at a temperature of less than about 50° C. during the step of adding (e.g., less than about 45° C., less than about 40° C., less than about 35° C., less than about 30° C., less than about 25° C., etc.). In some embodiments, the aqueous solution comprising a viral antigen is kept at a temperature range between about 25° C. and about 50° C. In some embodiments, the aqueous solution comprising a viral antigen is kept at room temperature.

In certain embodiments the vesicles are made by a process which includes steps of providing a lyophilized non-ionic surfactant (optionally with other components such as a steroid and/or an ionic amphiphile) and rehydrating the lyophilized non-ionic surfactant with an aqueous solution comprising a viral antigen such that antigen-containing vesicles are formed. The lyophilized non-ionic surfactant is prepared by melting the non-ionic surfactant (optionally with other components such as a steroid and/or an ionic amphiphile) to produce a molten mixture and then lyophilizing the molten mixture.

As described in more detail herein, in some embodiments, an immunogenic composition that includes a viral antigen formulated with vesicles may be lyophilized for future use and subsequently hydrated prior to use.

Vesicle Size and Processing

It will be appreciated that a vesicle composition will typically include a mixture of vesicles with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate vesicle formation and/or to alter vesicle particle size. In some embodiments, filtration, dialysis and/or centrifugation may be used to adjust the vesicle size distribution.

In general, vesicles produced in accordance with the methods of the present disclosure may be of any size. In certain embodiments, the composition may include vesicles with diameter in range of about 10 nm to about 10 μm. In certain embodiments, vesicles are of diameters between about 100 nm to about 5 μm. In certain embodiments, vesicles are of diameters between about 500 nm to about 2 μm. In certain embodiments, vesicles are of diameters between about 800 nm to about 1.5 μm. In some embodiments, the compositions may include vesicles with a diameter in the range of about 150 nm to about 15 μm. In certain embodiments, the vesicles may have a diameter which is greater than 10 μm, e.g., about 15 μm to about 25 μm. In certain embodiments, the vesicles may have a diameter in the range of about 0.1 μm to about 20 μm, about 0.1 μm to about 15 μm, about 0.1 μm to about 10 μm, about 0.5 μm to about 20 μm, about 0.5 μm to about 15 μm, about 0.5 μm to about 10 μm, about 1 μm to about 20 μm, about 1 μm to about 15 μm, or about 1 μm to about 10 μm. In certain embodiments, the vesicles may have a diameter in the range of about 2 μm to about 10 μm, e.g., about 1 μm to about 4 μm. In certain embodiments, the vesicles may have a diameter which is less than 150 nm, e.g., about 50 nm to about 100 nm Lyophilization Liquid formulation of vaccines has been the default presentation since the introduction of vaccines. Most of the existing liquid vaccine compositions have been developed for storage under refrigeration, but not at higher temperatures, with the result that their stability may not be optimal. In some cases, licensed vaccines are currently formulated and stored as liquids. In the aqueous environment the viral antigens are subjected to physical and chemical degradation that may lead to inactivation and loss of potency.

As discussed above, the methods of the present disclosure may include a step of lyophilizing a solution of a non-ionic surfactant (optionally with other components such as a steroid and/or an ionic amphiphile). Lyophilization is an established method used to enhance the long-term stability of products. Enhancement of physical and chemical stability is thought to be accomplished by preventing degradation and hydrolysis. Lyophilization involves freezing the preparation in question and then reducing the surrounding pressure (and optionally heating the preparation) to allow the frozen solvent(s) to sublime directly from the solid phase to gas (i.e., drying phase). In certain embodiments, the drying phase is divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. It will be appreciated that the freezing and drying phases are not necessarily distinct phases but can be combined in any manner. For example, in certain embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized product is optionally sealed.

In some embodiments, the lyophilized product is substantially free of organic solvent(s).

Excipients such as sucrose, amino acids or proteins such as gelatin or serum albumin may be used to protect the antigen during the drying process and storage. In some embodiments, a lyoprotectant may be used to protect antigens during lyophilization. Exemplary lyoprotectants include sucrose, trehalose, polyethylene glycol (PEG), dimethyl-succinate buffer (DMS), bovine serum albumin (BSA), mannitol, sorbitol, and dextran. Any suitable amount and/or combination of lyoprotectant(s) may be used to protect the antigen. For example, as demonstrated in U.S. Pat. No. 6,290,967, the dual presence of a disaccharide (e.g., sucrose) and a 6-carbon polyhydric alcohol (e.g., a sorbitol) enhanced the stability of a vaccine composition compared to control compositions. Sucrose was added in an amount ranging from 10 to 70 grams per liter of vaccine, and sorbitol was added in an amount ranging from about 15 to 90 grams per liter of vaccine.

Rehydration

Once a solution has been lyophilized, the methods of the present disclosure may include a step of rehydrating the lyophilized product to form antigen-containing vesicles. In some embodiments, this is achieved by mixing the lyophilized product with an aqueous solution comprising a viral antigen. In some embodiments, this involves adding the aqueous solution to the lyophilized product.

In some embodiments, the antigen-containing vesicles contain at least about 10% of the viral antigen added in the step of rehydrating. In some embodiments, the antigen-containing vesicles contain at least about 20% of the viral antigen added in the step of rehydrating. In some embodiments, the antigen-containing vesicles contain at least about 30% of the viral antigen added in the step of rehydrating. In some embodiments, the antigen-containing vesicles contain at least about 40% of the viral antigen added in the step of rehydrating. In some embodiments, the antigen-containing vesicles contain at least about 50% of the viral antigen added in the step of rehydrating. In some embodiments, the antigen-containing vesicles contain at least about 60% of the viral antigen added in the step of rehydrating. In some embodiments, the antigen-containing vesicles contain at least about 70% of the viral antigen added in the step of rehydrating. In some embodiments, the antigen-containing vesicles contain at least about 80% of the viral antigen added in the step of rehydrating. In some embodiments, the antigen-containing vesicles contain at least about 90% of the viral antigen added in the step of rehydrating.

In some embodiments, the aqueous solution includes a buffer. The buffer used will typically depend on the nature of the viral antigen or antigens in the aqueous solution. For example, without limitation, a PCB buffer, an $Na_2HPO_4$/$NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

In some embodiments, a composition of antigen-containing vesicles may be lyophilized for future use and subsequently hydrated (e.g., with sterile water or an aqueous buffer) prior to use. In some embodiments, a composition of antigen-containing vesicles may be stored at −80° C. prior to lyophilization.

In certain embodiments, the rehydrated immunogenic composition exhibits substantially the same potency as the immunogenic composition prior to lyophilization.

In some embodiments, the rehydrated immunogenic composition exhibits at least about 50% of the potency as the immunogenic composition prior to lyophilization (e.g., at least about 55%, 60%, 65%, 70%, 75%, 80%, 85%, 90%, 95% or 99%). In some embodiments, the level of potency is based on measurements obtained using an in vitro microtitration assay ($TCID_{50}$ Assay). In some embodiments, the level of potency is based on a plaque assay measurement.

In some embodiments, the rehydrated immunogenic composition exhibits at least 1.5 fold greater potency as compared to an otherwise equivalent immunogenic composition that was formulated without NISV (e.g., at least about 2 fold, 2.5 fold, 3 fold, 3.5 fold, 4 fold or 5 fold). In some embodiments, the level of potency is based on measurements obtained using an $TCID_{50}$ Assay. In some embodiments, the level of potency is based on a plaque assay measurement.

Storage

In certain embodiments, the lyophilized immunogenic composition may be stored for a period of time (e.g., days, weeks or months) prior to rehydration and administration to a subject in need thereof. In certain embodiments, the lyophilized immunogenic composition is exposed to temperatures in excess of 8° C. during storage (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., room temperature, etc.). In certain embodiments, the lyophilized immunogenic composition is stored under conditions that are not temperature controlled.

In certain embodiments, the lyophilized immunogenic compositions are thermostable in that the potency of the immunogenic composition remains substantially unchanged during storage despite being exposed to temperatures in excess of 8° C. (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., 37° C., room temperature, etc.) for a period of 1 to 6 months (e.g., 1, 2, 3, 4, 5 or 6 months, 12 weeks, etc.).

In certain embodiments, storage of the lyophilized immunogenic composition at these elevated temperatures destroys less than 20% of the potency of the viral antigen (e.g., less than 15%, less than 10%, less than 5%, less than 1%) as measured in an $TCID_{50}$ assay and as compared to an equivalent lyophilized immunogenic composition that was stored between 2 and 8° C. for the same time period.

In certain embodiments, the potency of the antigen post-storage is at least 1.5 fold greater than in an otherwise equivalent lyophilized immunogenic composition that was stored under the same elevated temperatures but that was formulated without NISV (e.g., at least about 2 fold, 2.5 fold, 3 fold, 3.5 fold, 4 fold or 5 fold). In some embodiments, the level of potency is based on measurements obtained using an $TCID_{50}$ assay. In some embodiments, the level of potency is based on plaque assay measurements.

In some embodiments, one or more of these potency results are obtained when the lyophilized immunogenic composition is stored at 25° C. for 1, 2, 3, 4, 5 or 6 months. In some embodiments, these results are obtained when the lyophilized immunogenic composition is stored at 15° C., 20° C., 30° C., 35° C., 37° C. or 40° C. for 1 month. In some embodiments, these results are obtained when the lyophilized immunogenic composition is stored at 15° C., 20° C., 30° C., 35° C., 37° C. or 40° C. for 2 months. In some embodiments, these results are obtained when the lyophilized immunogenic composition is stored at 15° C., 20° C., 30° C., 35° C., 37° C. or 40° C. for 3 months (or 12 weeks). In some embodiments, these results are obtained when the lyophilized immunogenic composition is stored at 15° C., 20° C., 30° C., 35° C., 37° C. or 40° C. for 4 months. In some embodiments, these results are obtained when the lyophilized immunogenic composition is stored at 15° C., 20° C., 30° C., 35° C., 37° C. or 40° C. for 5 months. In some embodiments, these results are obtained when the lyophilized immunogenic composition is stored at 15° C., 20° C., 30° C., 35° C., 37° C. or 40° C. for 6 months. In certain embodiments these temperatures may be allowed to vary within a range, e.g., ±2° C.

IV. Dosage and Administration

The compositions and methods of this disclosure are useful for treating viral infections in humans including adults and children. In general, however, compositions and methods of the present disclosure may be used with any animal. In certain embodiments, compositions and methods herein may be used for veterinary applications, e.g., canine and feline applications. If desired, compositions and methods herein may also be used with farm animals, such as ovine, avian, bovine, porcine and equine breeds.

Compositions described herein will generally be administered in such amounts and for such a time as is necessary or sufficient to induce an immune response. Dosing regimens may consist of a single dose or a plurality of doses over a period of time. The exact amount of an immunogenic composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In certain embodiments, the dose of viral antigen in an immunogenic composition is sufficient to yield $TCID_{50}$ values that are comparable to those in a licensed vaccine. For example, the licensed M-M-R-II® vaccine includes at least 1000 $TCID_{50}$ measles virus, at least 5000 $TCID_{50}$ mumps virus and at least 1000 $TCID_{50}$ rubella virus. $TCID_{50}$ (50% tissue culture infectious dose) quantifies the amount of virus required to infect 50% of inoculated tissue culture cells. Typically, $TCID_{50}$ values are measured by plating host cells (e.g., Vero cells) and adding serial dilutions of the viral antigen. After incubation, the percentage of infected cells is manually observed and recorded for each virus dilution, and results are used to mathematically calculate a $TCID_{50}$ value, e.g., according to the Behrens-Kärber method (Karber, *Arch Exp Pathol Pharmakol* 162:480-483, 1931).

In certain embodiments, the viral antigen is taken from a licensed human viral vaccine and the immunogenic composition is administered to a human at a dose that is less than the standard human dose (e.g., in the range of 10-90%, 10-80%, 10-70%, 10-60%, 10-50%, 10-40%, 10-30%, 10-20%, 20-90%, 20-80%, 20-70%, 20-60%, 20-50%, 20-40%, 20-30%, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, or 80-90% of the standard human dose).

In certain embodiments the immunogenic composition is administered as a single dose. In certain embodiments the immunogenic composition is administered as more than one dose (e.g., 1-3 doses that are separated by 1-12 months).

In certain embodiments, the compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for intramuscular delivery. In certain embodiments, the compositions may be formulated for subcutaneous delivery. For such parenteral administration, the compositions may be prepared and maintained in conventional lyophilized compositions and reconstituted prior to administration with a pharmaceutically acceptable saline solution, such as a 0.9% saline solution. The pH of the injectable composition can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

EXAMPLES

The following examples describe some exemplary modes of making and practicing certain compositions that are described herein. It should be understood that these examples are for illustrative purposes only and are not meant to limit the scope of the compositions and methods described herein.

Example 1: Two-Step Inverted Melt Method for Preparing Viral Antigen-Containing Vesicles This example describes a two-step inverted melt method that was used to prepare viral antigen-containing vesicles.

In Step 1, a 5:4:1 molar ratio of the following lipids: 1-monopalmitoyl glycerol (MPG), cholesterol (CHO) and dicetyl phosphate (DCP) was placed in a flat bottom 50 ml glass beaker, ensuring none of the powder stuck to the side of the glass beaker. The lipids were melted in a heated oil bath at about 120° C. for 10 minutes, with occasional swirling in the glass beaker covered with aluminum foil.

At this stage, a stock solution of M-M-R-II® vaccine (measles, mumps and rubella virus vaccine, live attenuated, Merck Frosst Std.) was pre-incubated for 5 minutes at about 30° C. in a heated water bath. In Step 2, the resulting M-M-R-II® vaccine stock solution was homogenized at an appropriate speed (e.g., at 8,000 rpm), the molten lipid mixture was added into the homogenizing M-M-R-II® vaccine stock solution, and homogenization was continued for a further 30 seconds at about 30° C. The resulting homogenate was shaken for 30 minutes at 220 rpm and about 30° C. An equivalent volume of a 400 mM sucrose solution in 25 mM sodium bicarbonate buffer (pH 9.7) was added to the shaken homogenate and the homogenate was further shaken for 5 minutes at 220 rpm at about 30° C. This mixture was aliquoted and frozen at −80° C., then lyophilized and reconstituted with 0.5 ml of sterile water for injection (WFI) prior to use. Compositions were prepared to give a total lipid concentration of 12.5 mg/ml.

In order to assess the thermostability of the reformulated M-M-R-II® vaccines, lyophilized aliquots were stored (prior to reconstitution) at two different thermal storage temperatures (25° C. and 40° C.) or the recommended 4° C. storage temperature for the unformulated commercial M-M-R-II® vaccine for a period of two weeks (n=3 at each temperature). A reformulated M-M-R-II® vaccine control that was prepared as above but without addition of NISVs was also tested. After 1 week and 2 weeks the stored samples were visually inspected for appearance, color and extent of caramelization of the lyophilized cake. The following Table 3 presents the results of this visual inspection. Some visible changes in appearance were observed for the lyophilized cake of the reformulated M-M-R-II® vaccine stored at 40° C. but no changes were observed in either color or extent of caramelization of the cake irrespective of storage temperature.

TABLE 3

| Group | Lipid mg/ml | Storage Temp | Visual observations | | |
|---|---|---|---|---|---|
| | | | | Week 1 | Week 2 |
| 1 | 12.5 | 4° C. | Appearance: | Normal | Normal |
| | | | Color: | Normal | Normal |
| | | | Caramelization: | No | No |
| 2 | 12.5 | 25° C. | Appearance: | Normal | Normal |
| | | | Color: | Normal | Normal |
| | | | Caramelization: | No | No |
| 3 | 12.5 | 40° C. | Appearance: | Mild crack-2 Mild Collapse-1 | Moderate Crack-1 Mild-Moderate Collapse-2 |
| | | | Color: | Normal | Normal |
| | | | Caramelization: | No | No |
| 4 | — | 4° C. | Appearance: | Normal | Normal |
| | | | Color: | Normal | Normal |
| | | | Caramelization: | No | No |
| 5 | — | 25° C. | Appearance: | Normal | Normal |
| | | | Color: | Normal | Normal |
| | | | Caramelization: | No | No |
| 6 | — | 40° C. | Appearance: | Normal | Mild Collapse-3 |
| | | | Color: | Normal | Normal |
| | | | Caramelization: | No | No |

Example 2: Measles Potency Assays ($TCID_{50}$ and Plaque)

A common test method that is used to quantitate the number of infectious particles in live virus vaccines is the 50% Tissue Culture Infective Dose ($TCID_{50}$) assay. This endpoint dilution assay quantifies the amount of virus required to kill 50% of infected hosts or to produce a cytopathic effect in 50% of inoculated tissue culture cells. This assay may be more common in clinical research applications where the lethal dose of virus must be determined or if the virus does not form plaques (see discussion of alternative plaque assay below). In the context of tissue culture, host cells are plated and serial dilutions of the virus are added. After incubation, the percentage of cell death (i.e., infected cells) is manually observed and recorded for each virus dilution, and results are used to mathematically calculate a $TCID_{50}$ result. Due to distinct differences in assay methods and principles, $TCID_{50}$ and pfu/ml (plaque assay result) or other infectivity assay results are not equivalent. This method can take up to a week due to cell infectivity time.

Vero cells were used in these experiments to assess the potency of the measles viruses in the reformulated M-M-R-II® vaccines. Reformulated M-M-R-II® vaccines prepared in accordance with Example 1 were reconstituted after a period of storage (discussed below) in water for injection. Vero cells were grown to 80% confluency in 96-well plates. 100 μl of tenfold dilutions of the reformulated vaccine were added to wells starting with a 1/10 dilution and doing seven additional 10 fold serial dilutions of the reformulated M-M-R-II® vaccines in culture medium. The virus titer quantifies the amount of virus required to produce a cytopathic effect in 50% of inoculated tissue culture cells. In order to assess the thermostability of the reformulated M-M-R-II® vaccines, lyophilized aliquots were stored for 2 weeks (prior to reconstitution) at three different temperatures (4° C., 25° C. and 40° C.). Measles virus titer ($TCID_{50}$) was determined after reconstitution as discussed above and the results are shown in FIG. 1. For the reformulated commercial vaccine control (homogenized and lyophilized in sucrose but lacking NISVs) virus titer fell off significantly for the aliquots stored at 40° C. in comparison to aliquots stored at 4° C. and 25° C. Aliquots of NISV formulated M-M-R-II® vaccine showed some loss of virus titer when stored at 40° C. but not to the same extent as the reformulated commercial vaccine control.

As mentioned above, another common test method that is used to quantitate the number of infectious particles in live virus vaccines is the plaque assay. This test method is based on the cytopathic effect of the virus in the vaccine on a susceptible cell line and is an in vitro measure of the potency of the vaccine composition (Schalk et al., *Journal of Virological Methods* 117:179-187, 2004).

Reformulated M-M-R-II® vaccines prepared in accordance with Example 1 are reconstituted after a period of storage (e.g., as discussed above) in water for injection. Since the M-M-R-II® vaccine is a trivalent vaccine, mumps and rubella viruses in the vaccine are initially neutralized by the addition of anti-mumps and anti-rubella antiserum followed by incubation at 4° C. for one hour (the antisera are heat-inactivated at 56° C. for 30 minutes prior to addition). 100, 500, 1000, 2500 and 5000-fold serial dilutions of the reformulated M-M-R-II® vaccines in culture medium are then prepared. Vero cells are grown to 90% confluency in 6-well plates. One day before infection, culture medium is refreshed. Cells are infected with 200 μl of each dilution (12 wells per dilution). After absorption of the virus for 45 minutes at room temperature, cells receive a 4 ml agar-overlay consisting of medium M199 (BioWhittaker Europe) with 4.7% inactivated fetal calf serum (Invitrogen), 0.11% $NaHCO_3$ and 0.33% agar. The plates are inverted and incubated at 36° C. and 2.5% $CO_2$. After 9 days, the agar-overlay is removed and cells are fixed in 96% ethanol for 2 minutes. Subsequently, cells are stained in carbol fuchsin and dried. Plaques are generally counted manually and results, in combination with the dilution factor used to prepare the plate, are used to calculate the number of plaque forming units per sample unit volume (pfu/ml). The pfu/ml result represents the number of infective particles within the sample and is based on the assumption that each plaque formed is representative of one infective virus particle.

Example 3: Viral Antigen-Containing Vesicles, Effect of Lipid Concentration on Thermostability and Liquid Stability This study was designed to evaluate the stabilization of nonionic surfactant vesicles (NISVs) containing live attenuated M-M-R-II® formulated with different lipid concentrations, buffers and sucrose using the inverted melt process as described in Example 1. The reformulated samples were stored at 5±3° C. and 37±2° C. The commercial vaccine M-M-R-II® was used as a positive control for comparison. The $TCID_{50}$ was used as an in vitro test (as described in Example 2) to determine the vaccine potency following 1, 2 and 12 weeks of storage. The results were compared to the performance of the commercial vaccine to evaluate the thermostable benefit of the reformulated samples.

A 5:4:1 molar ratio of the lipids: monopalmitoyl glycerol (MPG), cholesterol (CHO) and dicetyl phosphate (DCP) were placed in the bottom of a flat bottom glass beaker. The lipids were melted in an oil bath at 120° C.-122° C. with occasional mixing. M-M-R-II® vaccine (reconstituted with supplied diluents) was warmed at 30° C.-32° C. for 5 minutes. The M-M-R-II® vaccine solution was homogenized at 8000 rpm and the melted lipids were immediately transferred into the sample solution, and warmed at 30°

C.-32° C. After homogenization (30 seconds for TA 1-7 and 10-12), the resulting mixture was mixed for 30 minutes at 220 rpm at 30° C.-32° C. For certain samples, an equivalent volume of 400 mM sucrose solution, optionally prepared with 25 mM of bicarbonate buffer or sterile water, was then added. The prepared sample solution was mixed for another 5 minutes at 220 rpm at 30° C.-32° C. For TA 4, a concentrated phosphate buffer was added to M-M-R-II® vaccine solution prior to adding melted lipid. The solution was aliquoted into 1.0 mL aliquots/vial (TA 1-4, 10, 11) and 0.5 mL (TA 5-7 and 12) followed by lyophilization. The lyophilized vials were stored at 5±3° C. and 37±2° C. Each vial of the lyophilized samples was reconstituted with 1.0 mL of sterile water prior to Tissue Culture Infectious $Dose_{50}$ ($TCID_{50}$) analysis. The samples for this stability are as described in the following Table 4.

TABLE 4

| | | | Excipients | | | |
|---|---|---|---|---|---|---|
| TA# | Antigen | Lipid (mg/mL) | Sucrose (mM) | Conc. Phosphate Buffer (mM) | Bicarbonate Buffer** (mM) | Fill Volume/Vial Size |
| 1 | M-R-II ® | 25 | 400 | — | 25 | 1 mL/6 cc |
| 2 | M-R-II ® | 12.5 | 400 | — | 25 | 1 mL/6 cc |
| 3 | M-R-II ® | 3.125 | 400 | — | 25 | 1 mL/6 cc |
| 4 | M-R-II ® | 12.5 | 400 | 50* | — | 1 mL/6 cc |
| 5 | M-R-II ®* | 25 | — | — | — | 0.5 mL/2 cc |
| 6 | M-R-II ® | 12.5 | — | — | — | 0.5 mL/2 cc |
| 7 | M-R-II ® | 3.125 | — | — | — | 0.5 mL/2 cc |
| 10 | M-R-II ® | No NISV | 400 | — | 25 | 1 mL/6 cc |
| 11 | M-R-II ® | No NISV | 400 | 50* | — | 1 mL/6 cc |
| 12 | M-R-II ® | No NISV | — | — | — | 0.5 mL/2 cc |
| 13 | M-R-II ® | — | — | — | — | 0.5 mL/2 cc |

*Phosphate buffer was used to buffer M-R-II ® vaccine prior to lipid addition.
**25 mM Sodium Bicarbonate pH 9.7 was used to dissolve 400 mM Sucrose and added to samples prior to lyophilisation The lyophilized samples were collected from the temperature chamber. All samples were coded and stored at 4° C. before testing. The potency of measles component was determined with an in vitro microtitration assay. The $TCID_{50}$ assay estimated viable virus using a streamlined endpoint dilution assay that was analyzed statistically. Briefly, serial dilutions of these samples and the reference standard preparations were inoculated in rows of 10 wells of microtitre plates, together with Vero cells (African green monkey kidney epithelial cells; ATCC-CCL 81) used for 1, 2 and 12 week sample. The Vero cell line was initiated from the kidney of a normal adult African green monkey. The microtitre plates were inoculated with 50 μL of Vero cells in order to obtain $4.0\times10^5$ cells/mL titre in 24 hrs at 5% $CO_2$/37° C. (75-80% cell confluence is expected in these conditions). Each sample was reconstituted with 1000 μl of sterile distilled water, mixed for 15 seconds by hand followed with vortex for 45 seconds on medium speed (setting 5). The reconstituted samples (4 vials per time point) were transferred to the microtitre plates within 5 minutes in undiluted and diluted form ($10^{-1}$ to $10^{-7}$) on a 96-well plate in quadruplicates (100 μL/well). Dilutions $10^{-1}$ to $10^{-7}$ were prepared in 24-well plates completed with 5% FBS supplemented IMDM media and 100 μL was added to individual wells in quadruplicates. Positive and negative controls were included (in house processed commercial vaccine/commercial vaccine and cells, respectively). The plates were incubated at 35° C./5% $CO_2$ for 5 days. At the end of the incubation period, the numbers of the specific viral cytopathic effect (CPE) were counted and recorded. The $TCID_{50}$ per human dose was calculated according to these criteria. $TCID_{50}$ values were used to derive the geometric mean titres for statistical analysis.

For statistical analysis of all the samples, the transformed variables were related by using Prism 5 for windows (GraphPad Software, San Diego, Calif.) software to perform two tailed unpaired t-test and detect p-value between the groups. Statistical significance is indicated by a p-value between 0.05 to 0.01 and high statistical significance is indicated by a p-value less than 0.01. $TCID_{50}$ values were manipulated if the titer was identical for all the experiments in one group, such that the titre was rounded to the fourth decimal point to avoid the software limitation for nonparametric statistical analysis.

Figure 2:
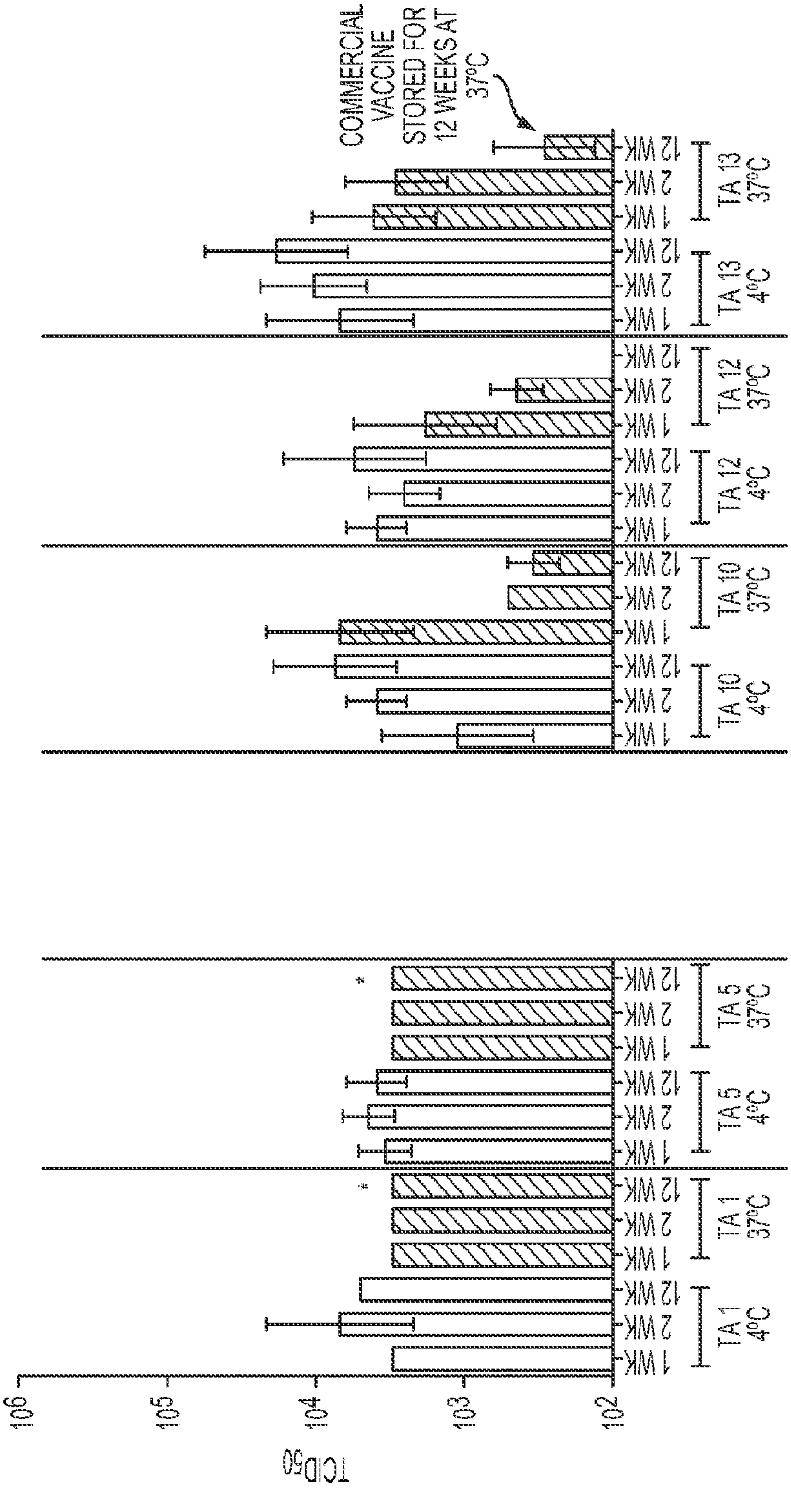
FIG. 2 shows exemplary results from a measles potency assay ($TCID_{50}$) that was performed using different reformulated M-M-R-II® vaccines (formulated with 25 mg/ml lipid) that had been stored at about 4° C. and about 37° C. for 1, 2 and up to 12 weeks.
Figure 3:
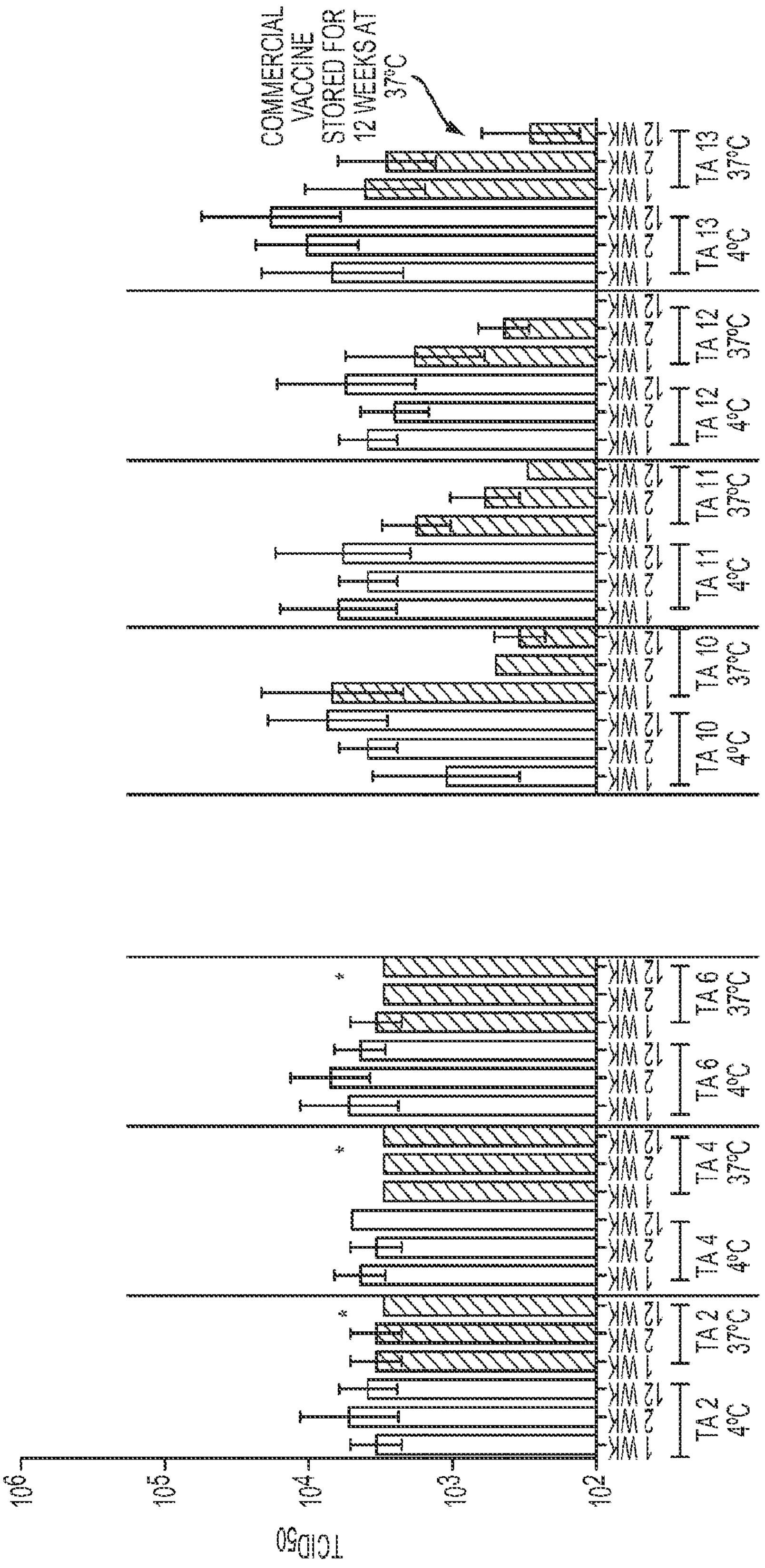
FIG. 3 shows exemplary results from a measles potency assay ($TCID_{50}$) that was performed using different reformulated M-M-R-II® vaccines (formulated with 12.5 mg/ml) that had been stored at about 4° C. and about 37° C. for 1, 2 and up to 12 weeks.
Figure 4:
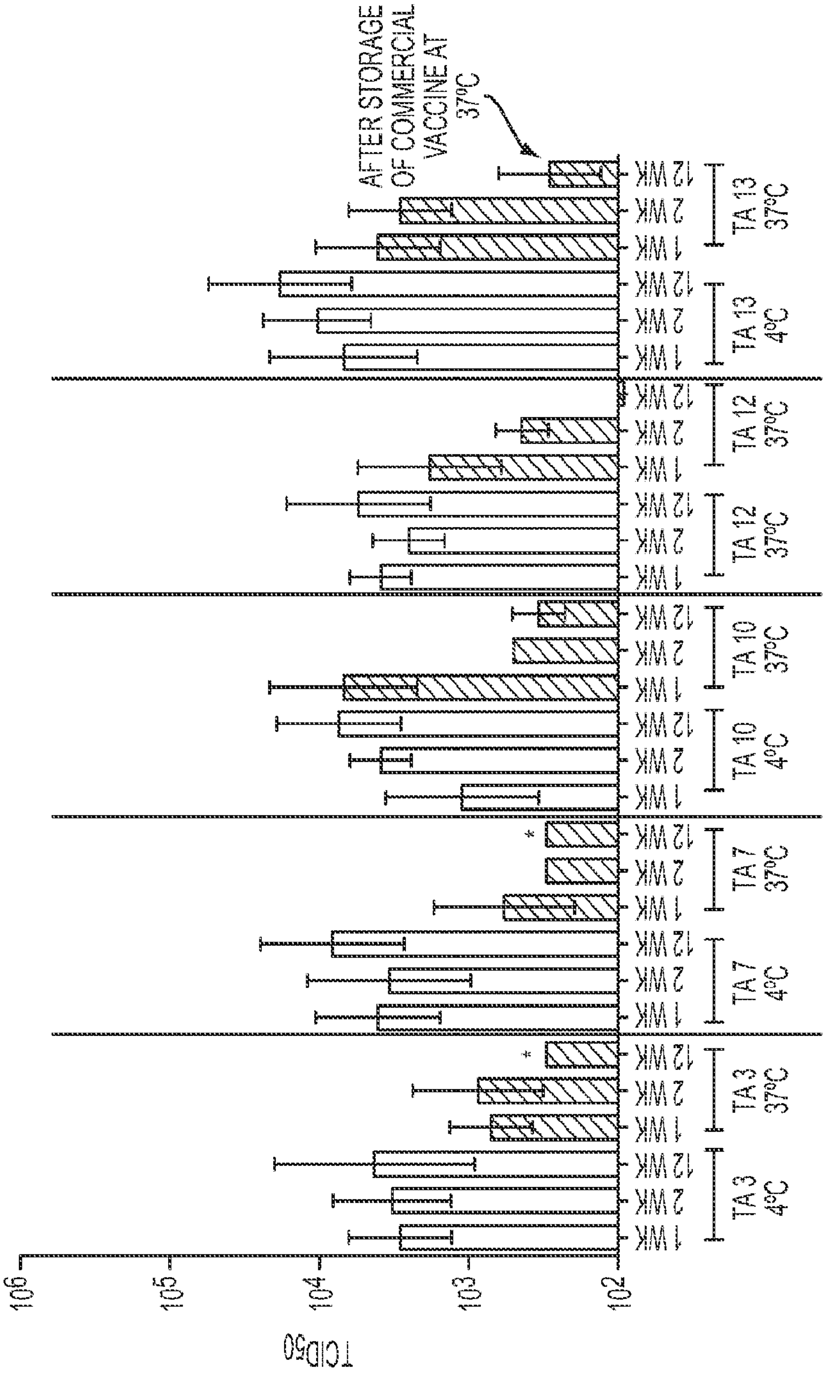
FIG. 4 shows exemplary results from a measles potency assay ($TCID_{50}$) that was performed using different reformulated M-M-R-II® vaccines (formulated with 3.125 mg/ml) that had been stored at about 4° C. and about 37° C. for 1, 2 and up to 12 weeks.

In FIG. 2 is shown the $TCID_{50}$ assay results of the samples (TA 1, 5 and 8) formulated with 25 mg/mL lipid, process controls TA 10 and TA12 (commercial vaccines exposed to all processing steps without lipid, with and without sucrose and buffer) and commercial vaccine (M-M-R-II®, TA 13) at both 5±3° C. and 37±2° C. The container closure system and the fill volume for TA 1 (1 mL of the reformulated proposed sample in 6 cc vials) was different compared to TA 5 (0.5 mL filled into a 2 cc vial) but results obtained for $TCID_{50}$ and physicochemical characterizations (data not shown) were comparable. The potency of TA 1 and 5 stored over 1, 2 and 12 weeks at 5±3° C. and 37±2° C. was higher than the limit advised by WHO (3.0 $log_{10}$) (FIG. 2). The reformulated samples with 25 mg/mL lipid did not show a loss in potency over 12 weeks when stored at higher temperature (37±2° C.) whereas the commercial vaccine potency decreased significantly ($p<0.0001$). The concentration of lipid appeared to affect the potency reading of the $TCID_{50}$ assay especially at the highest lipid concentration 25 mg/mL as indicated in FIGS. 2, 3 and 4. It was also observed that the non-lipid containing process control TA 10 and TA 12 were not stable for more than one week when stored at higher temperature (37±2° C.) (FIG. 2, TA 10). The TA 12 did not show stability at higher temperature after one week compared to the commercial vaccine which was stable up to two weeks at 37±2° C. but showed a decrease after 12 weeks. These results demonstrate a thermostable M-M-R-II® vaccine with a lipid concentration of 25 mg/mL (with or without sucrose and buffer) at elevated temperatures. At 5±3° C., the TA 1 and 5, the process controls (TA 10 and 12) and the commercial M-M-R-II® (TA 13) showed no loss in potency over 12 weeks of storage. TA 1 and 5 stored at 37±2° C., maintained higher potency compared to the commercial vaccine.

In FIG. 3 is shown the $TCID_{50}$ assay results of the samples (TA 2, 4, and 6) formulated with 12.5 mg/mL lipid, process control (commercial vaccines exposed to all processing steps without lipid, with and without sucrose and buffer) and commercial vaccine (M-M-R-II®) at both 5±3° C. and 37±2° C. The container closure system and the fill volume for TA 2 (1 ml of the reformulated proposed Test Article in 6 cc vials) was different compared to TA 6 (0.5 ml filled into 2 cc vials). The appearance of TA 6 was more consistent throughout the storage at higher temperature. The potency of TA 2, 4, and 6 stored over 1, 2 and 12 weeks at 5±3° C. and 37±2° C. was higher than the limit advised by WHO (3.0 $log_{10}$) (FIG. 3). The reformulated samples with 12.5 mg/mL lipid showed no loss in potency over 12 weeks storage at higher temperature (37±2° C.) whereas the commercial vaccine potency significantly decreased ($p<0.0001$). However, the concentration of lipid appeared to affect the potency reading of the TCID assay. The standard inverted melt method (TA 2, 4 and 6) showed comparable TCID results. It was also observed that the reformulated process control samples were not stable for more than one week when stored at higher temperature (37±2° C.) (FIG. 3 for TA 10 and TA 11). TA 12 did not show a loss in potency at higher temperature after one week compared to the commercial vaccine which was stable up to two weeks at 37° C. These results demonstrate a thermostable M-M-R-II® vaccine with the lipid concentration of 12.5 mg/ml. At 5±3° C., the samples (TA 2, 4, and 6), process control (no lipids) and the commercial vaccine showed stability up to 12 weeks. Samples formulated with NISVS (TA 2, 4, and 6) stored at both temperatures (5±3° C. and 37±2° C.) maintained higher potency compared to the 2 and 12 week old commercial vaccines.

In FIG. 4 is shown the $TCID_{50}$ assay results of the samples (TA 3 and 7) formulated with 3.125 mg/mL lipid, process control (commercial vaccines exposed to all processing steps without lipid, with and without sucrose and buffer like phosphate or bicarbonate buffer) and commercial vaccine (M-M-R-II®) at both 5±3° C. and 37±2° C. stability temperatures. The container closure system and the filled volume for TA 3 (1 mL of the reformulated proposed sample in 6 cc vial) was different compared to TA 7 (0.5 mL filled into 2 cc vials) but the appearance of TA 7 was more consistent throughout the storage at higher temperature. TA 3 and 7 contained the lowest lipid among all samples (3.125 mg/mL lipid) and showed the lowest potency even after 1 week of storage at 37±2° C. whereas the process control TA 10 and TA 11 showed no loss in potency after 1 week while the commercial vaccine showed no loss in potency over 2 weeks storage at 37±2° C. The potency of TA 3 and 7 stored over 1, 2 and 12 weeks at 37±2° C. was lower than the limit advised by WHO (3.0 $\log_{10}$) (FIG. 4). The reformulated samples with 3.125 mg/mL lipid did not show stability when stored at higher temperature (37±2° C.). It was also observed that the reformulated samples were not stable with or without sucrose or buffer (bicarbonate or phosphate) when stored at higher temperature (37±2° C.) (FIG. 4 for TA 10, TA 12 and TA 13). TA 12 did not show stability at higher temperature after one week compared to the commercial vaccine which was stable up to two weeks at 37±2° C. At 5±3° C., the proposed samples, process control and the commercial M-M-R-II® showed stability for up to 12 weeks. Samples containing 3.125 mg/mL of lipid were not stable when stored at elevated temperature (37±2° C.).

Figure 5:
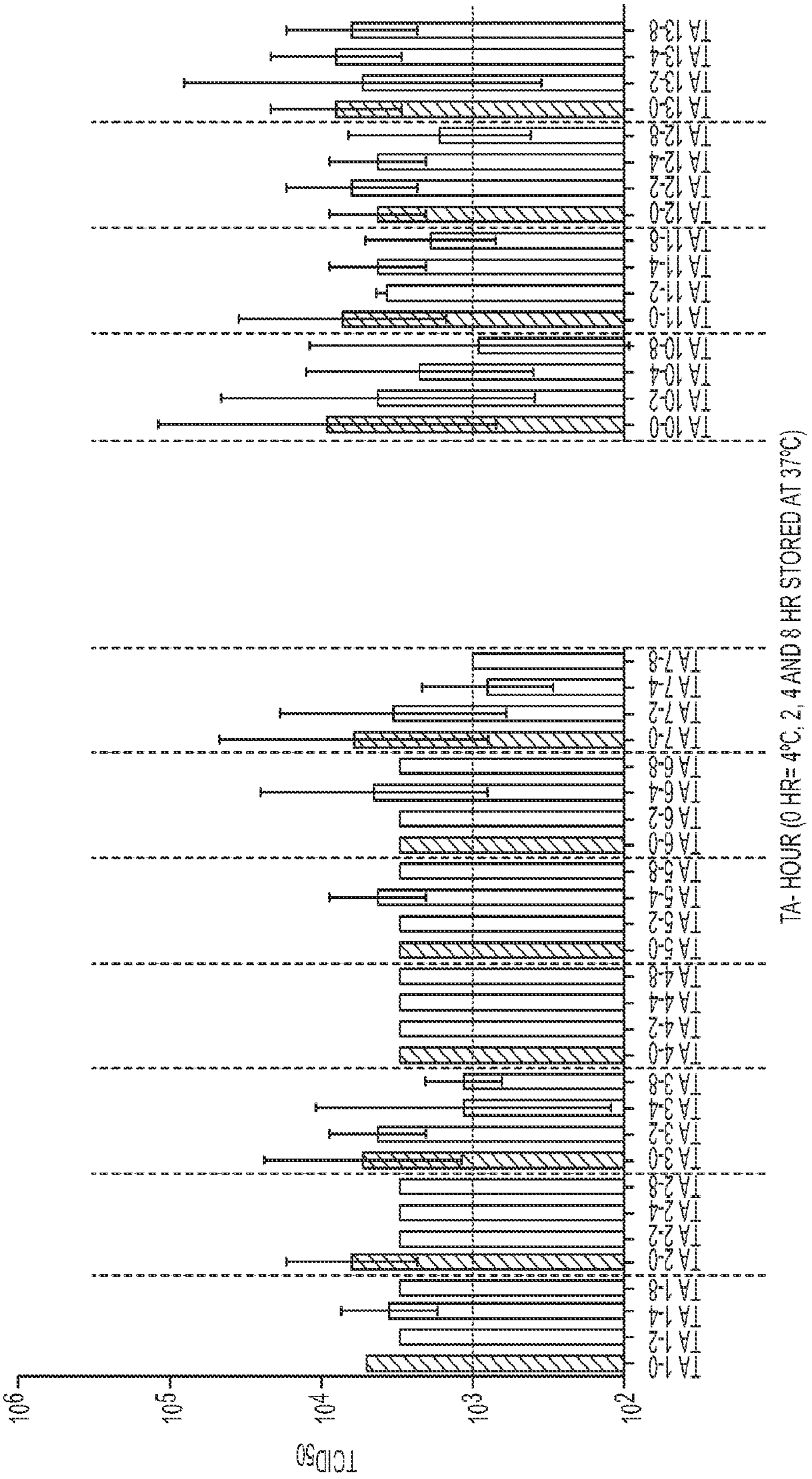
FIG. 5 shows exemplary results from a measles potency assay ($TCID_{50}$) that was performed using different reformulated M-M-R-II® vaccines that had been stored at about 4° C. for 4 weeks and then reconstituted and stored at about 37° C. for 2, 4 and up to hours to determine liquid stability.

To determine the effect of reformulation on liquid stability four week old samples stored at 4° C. were used to study the reconstituted (liquid) stability up to 8 hours at 37° C. temperature conditions. The samples were reconstituted with GIBCO water and kept at 37° C. for 8 hours. The samples were withdrawn for potency assay at the intervals of 0, 2, 4 and 8 hour. It is recommended that the reconstituted M-M-R-II® should be used as soon as possible after reconstitution or that reconstituted vaccine should be stored in the vaccine vial in a dark place at 2-8° C. and discarded if not used within 8 hours (The Immunological Basis for Immunization Series, Module 7: Measles (WHO/EPI/GEN/93.17). WHO has reported that at room temperature reconstituted vaccine loses about 50% efficacy in one hour and at 37° C. inactivation occurs within one hour. In FIG. 5 it is shown that reconstituted TA 1 with 25 mg/mL lipid concentration or TA 2 with 12.5 mg/mL lipid concentration had comparable potency compared to the commercial vaccine after 8 hours of storage at 37° C. (the difference was not significant). This liquid stability (FIG. 5) demonstrated that reformulated samples with lipid concentration of 3.125 mg/mL experienced a greater loss in potency compared to the samples prepared with 25 mg/mL or 12.5 mg/mL of lipids. The $TCID_{50}$ value of TA 3 and 7 were reduced after 2 hours of storage at 37° C.

In summary, the lyophilized samples containing M-M-R-II® vaccine in NISVs (12.5 or 25 mg/mL of lipid) prepared by inverted melt process had no change in potency over 12 weeks storage at 5±3° C. and 37±2° C. The highest lipid concentration tested 25 mg/mL did not appear to provide any additional benefit in maintaining potency compared to samples containing lower lipid concentration (12.5 mg/mL), however the present disclosure encompasses the use of higher concentrations. The samples prepared with 25 mg/mL or 12.5 mg/mL showed no loss in potency over eight hours following reconstitution. The addition of sucrose or buffer (phosphate or bicarbonate) did not show any additional benefit in preserving potency in the samples formulated with 25 mg/mL or 12.5 mg/mL lipid. The samples with the lowest lipid concentration (3.125 mg/mL) did not maintain potency when stored at 37° C. for 12 weeks.

OTHER EMBODIMENTS

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. A method of increasing thermostability of an immunogenic composition, the method comprising:

melting lipids comprising 1-monopalmitoyl glycerol, dicetyl phosphate and cholesterol to produce molten lipids;

combining the molten lipids with an aqueous solution comprising an attenuated virus, wherein said attenuated virus comprises an attenuated measles virus, an attenuated mumps virus, an attenuated rubella virus, an attenuated varicella virus, or a combination thereof;

homogenizing the resulting product to produce a homogenate comprising vesicles, wherein the molten lipids and aqueous solution are combined in relative amounts and volumes that achieve a lipid concentration of about 12.5 mg/ml to about 25 mg/ml in the homogenate;

and lyophilizing the homogenate to produce an immunogenic composition, thereby increasing the level of thermostability of the immunogenic composition, relative to a comparator composition having a lipid concentration of less than about 12.5 mg/ml to about 25 mg/ml, following storage of both the immunogenic composition and the comparator composition for 12 weeks at 37±2° C.

2. The method of claim 1, wherein the molten lipids are added to the aqueous solution comprising the attenuated virus.

3. The method of claim 1, wherein the aqueous solution comprising the attenuated virus is added to the molten lipids.

4. The method of claim 1, wherein at least a portion of the virus is associated with the vesicles.

5. The method of claim 1, wherein the virus is encapsulated within an aqueous core of the vesicles.

6. The method of claim 1, wherein the thermostable immunogenic composition lacks an alum adjuvant.

7. The method of claim 1, further comprising comparing at least one measure of thermostability of the immunogenic composition to at least one measure of thermostability of the comparator composition.

8. The method of claim 1, wherein the immunogenic composition exhibits less than 50% loss in potency as determined by a TCID50 assay when stored for 12 weeks at 37±2° C.

* * * * *